(12) United States Patent  (10) Patent No.: US 8,049,029 B2
Bruening et al.  (45) Date of Patent: Nov. 1, 2011

(54) PROCESS FOR PREPARING 2-AMINO-5-CYANOBENZOIC ACID DERIVATIVES

(75) Inventors: Joerg Bruening, Wilmington, DE (US); Gary David Annis, Landenberg, PA (US); Donald J Dumas, Wilmington, DE (US); Rafael Shapiro, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 141 days.

(21) Appl. No.: 12/516,807

(22) PCT Filed: Dec. 18, 2007

(86) PCT No.: PCT/US2007/025800
§ 371 (c)(1),
(2), (4) Date: May 29, 2009

(87) PCT Pub. No.: WO2008/082502
PCT Pub. Date: Jul. 10, 2008

(65) Prior Publication Data
US 2010/0280251 A1  Nov. 4, 2010

Related U.S. Application Data

(60) Provisional application No. 60/902,465, filed on Feb. 21, 2007, provisional application No. 60/876,394, filed on Dec. 21, 2006.

(51) Int. Cl.
C07C 253/00 (2006.01)
(52) U.S. Cl. ........................................ 558/343
(58) Field of Classification Search ................ None
See application file for complete search history.

(56) References Cited

U.S. PATENT DOCUMENTS

| 6,759,554 B2 * | 7/2004 | Buchwald et al. ............ 564/192 |
| 6,867,298 B2 * | 3/2005 | Buchwald et al. ............ 540/489 |
| 2004/0138468 A1 * | 7/2004 | Buchwald et al. ............ 546/290 |

FOREIGN PATENT DOCUMENTS

| WO | 2004/067528 | 8/2004 |
| WO | 2006/023783 | 3/2006 |
| WO | 2006/062978 | 6/2006 |
| WO | 2006/068669 | 6/2006 |
| WO | WO 2006062978 A1 * | 6/2006 |
| WO | WO 2006068669 A1 * | 6/2006 |
| WO | 2008/070158 | 6/2008 |

OTHER PUBLICATIONS

Zanon et al., Copper-Catalyzed Domino Halide Exchange-Cyanation of Aryl Bromides, J. Am. Chem. Soc. 2003, 125, pp. 2890-2891.

* cited by examiner

Primary Examiner — Janet Andres
Assistant Examiner — Heidi Reese
(74) Attorney, Agent, or Firm — Renee M. Lett

(57) ABSTRACT

Disclosed is a method for preparing a compound of Formula 1 comprising contacting a compound of Formula 2 with a metal cyanide reagent, a copper(I) salt reagent, an iodide salt reagent and at least one compound of Formula 3

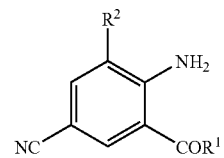

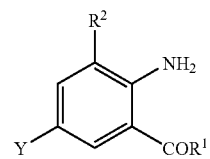

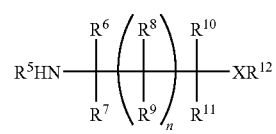

wherein $R^1$ is $NHR^3$ or $OR^4$; $R^2$ is $CH_3$ or Cl; $R^3$ is H, $C_1$-$C_4$ alkyl, cyclopropyl, cyclopropylcyclopropyl, cyclopropylmethyl or methylcyclopropyl; $R^4$ is H or $C_1$-$C_4$ alkyl; Y is Br or Cl; X is $NR^{13}$ or O; n is 0 or 1; and $R^5, R^6, R^7, R^8, R^9, R^{10}, R^{11}, R^{12}$ and $R^{13}$ are as defined in the disclosure.

Also disclosed is a method for preparing a compound of Formula 2 wherein Y is Br and $R^1$ is $NHR^3$ comprising introducing a gas containing bromine into a liquid containing a compound of Formula 4, and further disclosed is a method for preparing a compound of Formula 5 wherein $R^{14}, R^{15}, R^{16}$ and Z are as defined in the disclosure using a compound of Formula 1 characterized by preparing the compound of Formula 1 by the method disclosed above.

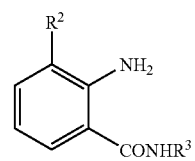

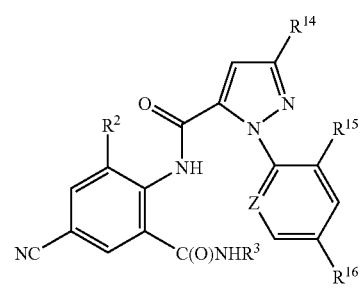

3 Claims, No Drawings

PROCESS FOR PREPARING 2-AMINO-5-CYANOBENZOIC ACID DERIVATIVES

FIELD OF THE INVENTION

The present invention pertains to a method for the preparation of 3-substituted 2-amino-5-cyanobenzoic acid derivatives.

BACKGROUND OF THE INVENTION

Preparation of certain 2-amino-5-cyanobenzoic acids and their utility as intermediates for preparing corresponding insecticidal cyanoanthranilic diamides has been disclosed (see e.g., Scheme 9 in PCT Patent Publication WO 2004/067528; Scheme 9 and Example 2, Step A in PCT Patent Publication WO 2006/068669; and Scheme 15 and Example 6, Step B in PCT Patent Publication WO 2006/062978).

However, the need continues for new or improved methods suitable for rapidly providing 2-amino-5-cyanobenzoic acid derivatives.

SUMMARY OF THE INVENTION

The present invention is directed to a method for preparing a compound of Formula 1

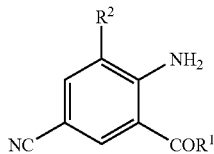

1 wherein
$R^1$ is $NHR^3$ or $OR^4$;
$R^2$ is $CH_3$ or Cl;
$R^3$ is H, $C_1$-$C_4$ alkyl, cyclopropyl, cyclopropylcyclopropyl, cyclopropylmethyl or methylcyclopropyl; and
$R^4$ is H or $C_1$-$C_4$ alkyl;
comprising contacting (I) a compound of Formula 2

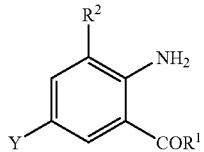

2 wherein Y is Br or Cl;
with (2) a metal cyanide reagent, (3) a copper(I) salt reagent, (4) an iodide salt reagent and (5) at least one compound of Formula 3

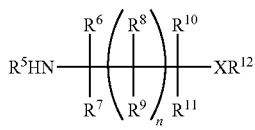

3 wherein
X is $NR^{13}$ or O;
$R^5$, $R^7$, $R^8$, $R^9$, $R^{11}$ and $R^{12}$ are independently H or $C_1$-$C_4$ alkyl;
$R^6$ and $R^{10}$ are independently H, $C_1$-$C_4$ alkyl or phenyl;
$R^{13}$ is H or methyl; and
n is 0 or 1;
provided that:
(i) when n is 0, X is $NR^{13}$, and $R^5$, $R^{12}$ and $R^{13}$ are H, then at least two of $R^6$, $R^7$, $R^{10}$ and $R^{11}$ are other than H;
(ii) when n is 1, X is $NR^{13}$, and $R^5$, $R^{12}$ and $R^{13}$ are H, then at least two of $R^6$, $R^7$, $R^8$, $R^9$, $R^{10}$ and $R^{11}$ are other than H;
(iii) when n is 0, X is O, and $R^5$ and $R^{12}$ are H, then at least two of $R^6$, $R^7$, $R^{10}$ and $R^{11}$ are other than H;
(iv) when n is 1, X is O, and $R^5$ and $R^{12}$ are H, then at least two of $R^6$, $R^7$, $R^8$, $R^9$, $R^{10}$ and $R^{11}$ are other than H; and
(v) when Y is Cl, then $R^2$ is methyl.

This invention also provides a method for preparing a compound of Formula 2

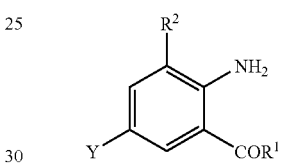

2 wherein
Y is Br;
$R^1$ is $NHR^3$;
$R^2$ is $CH_3$ or Cl; and
$R^3$ is H, $C_1$-$C_4$ alkyl, cyclopropyl, cyclopropylcyclopropyl, cyclopropylmethyl or methylcyclopropyl;
comprising introducing (a) a gas containing bromine into (b) a liquid containing a compound of Formula 4

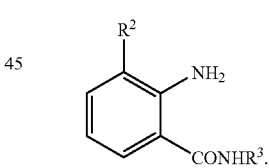

4

This invention also provides a method for preparing a compound of Formula 5

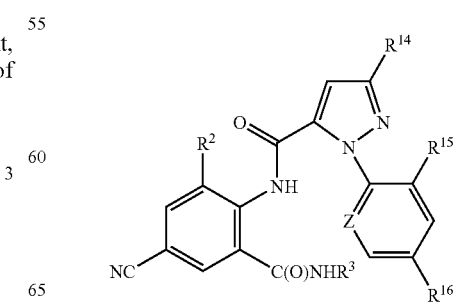

5 wherein
R² is CH₃ or Cl;
R³ is H, $C_1$-$C_4$ alkyl, cyclopropyl, cyclopropylcyclopropyl, cyclopropylmethyl or methylcyclopropyl;
Z is $CR^{17}$ or N;
$R^{14}$ is Cl, Br, $CF_3$, $OCF_2H$ or $OCH_2CF_3$;
$R^{15}$ is F, Cl or Br;
$R^{16}$ is H, F or Cl; and
$R^{17}$ is H, F, Cl or Br;
using a compound of Formula 1. The method characterized by preparing the compound of Formula 1 from the compound of Formula 2 by the method disclosed above.

Further related aspects of the present invention pertain to combinations of the aforedescribed methods, including a method for preparing a compound of Formula 5 comprising preparing a compound of Formula 2 as described above, then preparing a compound of Formula 1 from the compound of Formula 2 as described above, and then preparing the compound of Formula 5 using the compound of Formula 1.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are taste (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In some instances herein ratios are recited as single numbers, which are relative to the number 1; for example, a ratio of 4 means 4:1.

As used herein, the term cyanide equivalent when referring to a compound comprising one or more cyanide groups, relates to the number of cyanide ions ($CN^-$) per mole of the cyanide-containing compound. For example, a hexacyanoferrate(II) reagent has six cyanide ions per mole; therefore, if the cyanide equivalent ratio of a hexacyanoferrate(II) reagent relative to another reagent is 1:1, then the mole ratio would be 0.167:1.

In the above recitations, the term "alkyl" includes straight-chain or branched alkyl, such as, methyl, ethyl, butyl, n-propyl, i-propyl, or the different butyl isomers.

The term "cyclopropylcyclopropyl," denotes cyclopropyl substitution on a cyclopropyl ring. Examples of "cyclopropylcyclopropyl," include 1,1'-bicyclopropyl-1-yl, 1,1'-bicyclopropyl-2-yl and the different isomers such as (1R,2S)-1,1'-bicyclopropyl-2-yl and (1R,2R)-1,1'-bicyclopropyl-2-yl.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and 0 to 3 heteroatoms. Of note are carbon-based radicals selected from $C_1$-$C_4$ alkyl, $C_1$-$C_2$ haloalkyl and phenyl optionally substituted with 1-3 substituents selected from $C_1$-$C_3$ alkyl, halogen and nitro.

As referred to in the present disclosure, the term "carboxylic acid" means an organic chemical compound comprising at least one carboxylic acid functional group (i.e. —C(O)OH). The term "carboxylic acid" does not include the compound carbonic acid (i.e. HOC(O)OH). Carboxylic acids include, for example, formic acid, acetic acid, propionic acid, chloroacetic acid, benzoic acid, maleic acid and citric acid. The term "effective $pK_a$" refers to the $pK_a$ of the carboxylic acid functional group, or if the compound has more than one carboxylic acid functional group, "effective $pK_a$" refers to the $pK_a$ of the most acidic carboxylic acid functional group. As referred to herein, the "effective pH" of a nonaqueous substance or mixture, such as a reaction mixture, is determined by mixing an aliquot of the substance or mixture with about 5 to 20 volumes of water and then measuring the pH of the resulting aqueous mixture (e.g., with a pH meter). As referred to herein, a "substantially anhydrous" substance means the substance contains no more than about 1% water by weight. The chemical name "isatoic anhydride" is another name corresponding to the current Chemical Abstracts name "2H-3,1-benzoxazine-2,4(1H)-dione".

Embodiments of the present invention include:

Embodiment A1. The method described in the Summary of the Invention for preparing a compound of Formula 1 comprising contacting reagent (1) (i.e. a compound of Formula 2) with reagent (2) (i.e. a metal cyanide reagent) and reagent (3) (i.e. a copper(I) salt reagent), reagent (4) (i.e. an iodide salt reagent) and reagent (5) (i.e. at least one compound of Formula 3).

Embodiment A2. The method of Embodiment A1 wherein $R^1$ is $NHR^3$.

Embodiment A3. The method of Embodiment A2 wherein $R^3$ is $C_1$-$C_4$ alkyl, cyclopropyl, cyclopropylcyclopropyl, cyclopropylmethyl or methylcyclopropyl.

Embodiment A4. The method of Embodiment A3 wherein $R^3$ is $C_1$-$C_4$ alkyl or cyclopropylmethyl.

Embodiment A5. The method of Embodiment A4 wherein $R^3$ is methyl.

Embodiment A6. The method of Embodiment A1 wherein Y is Br.

Embodiment A7. The method of Embodiment A1 wherein reagent (2) comprises one or more metal cyanides selected from the group consisting of alkali metal cyanides and alkali metal hexacyanoferrate(II).

Embodiment A8. The method of Embodiment A7 wherein reagent (2) comprises one or more metal cyanides selected from the group consisting of sodium cyanide, potassium cyanide, potassium hexacyanoferrate(II) and sodium hexacyanoferrate(II).

Embodiment A9. The method of Embodiment A8 wherein reagent (2) comprises one or more compounds selected from the group consisting of sodium cyanide, potassium cyanide and potassium hexacyanoferrate(II).

Embodiment A10. The method of Embodiment A9 wherein reagent (2) comprises sodium cyanide or potassium hexacyanoferrate(II).

Embodiment A11. The method of Embodiment A10 wherein reagent (2) comprises sodium cyanide.

Embodiment A12. The method of Embodiment A1 wherein the cyanide equivalent ratio of reagent (2) to reagent (1) is at least about 1.

Embodiment A13. The method of Embodiment A12 wherein the cyanide equivalent ratio of reagent (2) to reagent (1) is at least about 1.15.

Embodiment A14. The method of Embodiment A1 wherein the cyanide equivalent ratio of reagent (2) to reagent (1) is not larger than about 1.5.

Embodiment A15. The method of Embodiment A14 wherein the cyanide equivalent ratio of reagent (2) to reagent (1) is not larger than about 1.25.

Embodiment A16. The method of Embodiment A1 wherein n is 0.

Embodiment A17. The method of Embodiment A1 wherein X is $NR^{13}$.

Embodiment A18. The method of Embodiment A1 wherein $R^{13}$ is H.

Embodiment A19. The method of Embodiment A1 wherein $R^5$ is methyl or H.

Embodiment A20. The method of Embodiment A1 wherein $R^6$ and $R^{10}$ are H.

Embodiment A21. The method of Embodiment A1 wherein $R^7$ and $R^{11}$ are H.

Embodiment A22. The method of Embodiment A1 wherein $R^{12}$ is methyl or H.

Embodiment A23. The method of Embodiment A1 wherein n is 1.

Embodiment A24. The method of Embodiment A1 wherein $R^8$ and $R^9$ are each independently methyl or H.

Embodiment A25. The method of Embodiment A1 wherein reagent (5) comprises one or more compounds selected from the group consisting of N,N'-dimethylethylenediamine, N,N'-dimethyl-1,3-propanediamine and 2,2-dimethyl-1,3-propanediamine.

Embodiment A26. The method of Embodiment A25 wherein reagent (5) comprises N,N'-dimethylethylenediamine.

Embodiment A27. The method of Embodiment A1 wherein the mole ratio of reagent (5) to reagent (3) is at least about 1.

Embodiment A28. The method of Embodiment A27 wherein the mole ratio of reagent (5) to reagent (3) is at least about 2.

Embodiment A29. The method of Embodiment A28 wherein the mole ratio of reagent (5) to reagent (3) is at least about 4.

Embodiment A30. The method of Embodiment A1 wherein the mole ratio of reagent (5) to reagent (3) is not larger than about 10.

Embodiment A31. The method of Embodiment A30 wherein the mole ratio of reagent (5) to reagent (3) is not larger than about 6.

Embodiment A32. The method of Embodiment A1 wherein the mole ratio of reagent (3) to reagent (1) is at least about 0.01.

Embodiment A33. The method of Embodiment A32 wherein the mole ratio of reagent (3) to reagent (1) is at least about 0.1.

Embodiment A34. The method of Embodiment A33 wherein the mole ratio of reagent (3) to reagent (1) is at least about 0.15.

Embodiment A35. The method of Embodiment A1 wherein the mole ratio of reagent (3) to reagent (1) is less than about 1.

Embodiment A36. The method of Embodiment A1 wherein the mole ratio of reagent (3) to reagent (1) is not larger than about 0.99.

Embodiment A37. The method of Embodiment A36 wherein the mole ratio of reagent (3) to reagent (1) is not larger than about 0.5.

Embodiment A38. The method of Embodiment A37 wherein when Y is Cl then the mole ratio of reagent (3) to reagent (1) is not larger than about 0.4.

Embodiment A39. The method of Embodiment A38 wherein when Y is Cl then the mole ratio of reagent (3) to reagent (1) is not larger than about 0.3.

Embodiment A40. The method of Embodiment A37 wherein the mole ratio of reagent (3) to reagent (1) is not larger than about 0.25.

Embodiment A41. The method of Embodiment A40 wherein when Y is Br then the mole ratio of reagent (3) to reagent (1) is not larger than about 0.2.

Embodiment A42. The method of Embodiment A1 wherein the mole ratio of reagent (4) to reagent (1) is at least about 0.001.

Embodiment A43. The method of Embodiment A42 wherein the mole ratio of reagent (4) to reagent (1) is at least about 0.05.

Embodiment A44. The method of Embodiment A43 wherein the mole ratio of reagent (4) to reagent (1) is at least about 0.15.

Embodiment A45. The method of Embodiment A1 wherein the mole ratio of reagent (4) to reagent (1) is less than about 1.

Embodiment A46. The method of Embodiment A1 wherein the mole ratio of reagent (4) to reagent (1) is not larger than about 0.5.

Embodiment A47. The method of Embodiment A46 wherein when Y is Cl then the mole ratio of reagent (4) to reagent (1) is not larger than about 0.4.

Embodiment A48. The method of Embodiment A47 wherein when Y is Cl then the mole ratio of reagent (4) to reagent (1) is not larger than about 0.3.

Embodiment A49. The method of Embodiment A46 wherein when Y is Br then the mole ratio of reagent (4) to reagent (1) is not larger than about 0.2.

Embodiment A50. The method of Embodiment A1 wherein reagent (3) and reagent (4) comprise copper(I) iodide.

Embodiment A51. The method of Embodiment A1 wherein reagent (1), reagent (2), reagent (3), reagent (4) and reagent (5) are contacted in a suitable organic solvent.

Embodiment A52. The method of Embodiment A1 wherein reagent (1) is contacted with a suitable organic solvent to form a mixture, and then reagent (2), reagent (3), reagent (4) and reagent (5) are sequentially added to the mixture.

Embodiment A53. The method of any one of Embodiments A51 and A52 wherein the suitable organic solvent comprising one or more solvents selected from the group consisting of halogenated and nonhalogenated aliphatic and aromatic hydrocarbons.

Embodiment A54. The method of Embodiment A53 wherein the suitable organic solvent comprises one or more solvents selected from the group consisting of heptane, xylenes, toluene, chlorobenzene, 1,2,4-trimethylbenzene, 1,3,5-trimethylbenzene, ethylbenzene, (1-methylethyl)benzene (also known as cumene) and $C_1$-$C_3$ alkyl-substituted naphthalenes (e.g., 1-methylnaphthalene, 2-methylnaphthalene, 1,5-dimethylnaphthalene, 2,6-dimethylnaphthalene and 1,3-dimethylnaphthalene).

Embodiment A55. The method of Embodiment A54 wherein the suitable organic solvent comprises one or more solvents selected from the group consisting of xylenes, toluene, chlorobenzene, 1,2,4-trimethylbenzene, 1,3,5-trimethylbenzene and 1-methylnaphthalene.

Embodiment A56. The method of any one of Embodiments A51 and A52 wherein Y is Br and the suitable organic solvent comprises xylenes.

Embodiment A57. The method of any one of Embodiments A51 and A52 wherein Y is Cl and the suitable organic solvent comprises 1-methylnaphthalene.

Embodiment A58. The method of any one of Embodiments A51, A52, A53, A54, A55, A56 and A57 wherein the ratio of the volume of the suitable organic solvent to the weight of reagent (1) is at least about 2 mL/g.

Embodiment A59. The method of Embodiment A58 wherein the ratio of the volume of the suitable organic solvent to the weight of reagent (1) is at least about 3 mL/g.

Embodiment A60. The method of any one of Embodiments A51, A52, A53, A54, A55, A56 and A57 wherein the ratio of the volume of the suitable organic solvent to reagent (1) is not larger than about 10 mL/g.

Embodiment A61. The method of Embodiment A60 wherein the ratio of the volume of the suitable organic solvent to the weight of reagent (1) is not larger than about 6 mL/g.

Embodiment A62. The method of any one of Embodiments A51, A52, A53, A54, A55, A56 and A57 wherein the weight ratio of the suitable organic solvent to reagent (1) is at least about 2.

Embodiment A63. The method of Embodiment A62 wherein the weight ratio of the suitable organic solvent to reagent (1) is at least about 3.

Embodiment A64. The method of any one of Embodiments A51, A52, A53, A54, A55, A56 and A57 wherein the weight ratio of the suitable organic solvent to reagent (1) is not larger than about 10.

Embodiment A65. The method of Embodiment A64 wherein the weight ratio of the suitable organic solvent to reagent (1) is not larger than about 6.

Embodiment A66. The method of Embodiment A51 wherein reagent (1) is contacted with the suitable organic solvent to form a mixture, and reagent (2), reagent (3), reagent (4) and reagent (5) are sequentially added to the mixture, and then the mixture is purged with an inert gas.

Embodiment A67. The method of Embodiment A51 wherein reagent (1) is contacted with the suitable organic solvent to form a mixture, and reagent (2), reagent (3) and reagent (4) are sequentially added to the mixture, the mixture is purged with an inert gas, and then reagent (5) is added.

Embodiment A68. The method of Embodiment A51 wherein reagent (1), reagent (2), reagent (3), reagent (4) and reagent (5) are contacted with the suitable organic solvent, and the pressure is increased above atmospheric pressure and the temperature is increased above the boiling point of the solvent at atmospheric pressure.

Embodiment A69. The method of Embodiment A51 wherein when Y is Cl then reagent (1), reagent (2), reagent (3), reagent (4) and reagent (5) are contacted with the suitable organic solvent at a temperature not greater than about 200° C.

Embodiment A70. The method of Embodiment A69 wherein when Y is Cl then reagent (1), reagent (2), reagent (3), reagent (4) and reagent (5) are contacted with the suitable organic solvent at a temperature not greater than about 190° C.

Embodiment A71. The method of Embodiment A51 wherein reagent (1), reagent (2), reagent (3), reagent (4) and reagent (5) are contacted with the suitable organic solvent at a temperature not greater than about 170° C.

Embodiment A72. The method of Embodiment A71 wherein reagent (1), reagent (2), reagent (3), reagent (4) and reagent (5) are contacted with the suitable organic solvent at a temperature not greater than about 160° C.

Embodiment A73. The method of Embodiment A51 wherein reagent (1), reagent (2), reagent (3), reagent (4) and reagent (5) are contacted with the suitable organic solvent at a temperature greater than about 115° C.

Embodiment A74. The method of Embodiment A73 wherein reagent (1), reagent (2), reagent (3), reagent (4) and reagent (5) are contacted with the suitable organic solvent at a temperature greater than about 120° C.

Embodiment A75. The method of Embodiment A74 wherein when Y is Br then reagent (1), reagent (2), reagent (3), reagent (4) and reagent (5) are contacted with the suitable organic solvent at a temperature greater than about 125° C.

Embodiment A76. The method of Embodiment A75 wherein when Y is Br then reagent (1), reagent (2), reagent (3), reagent (4) and reagent (5) are contacted with the suitable organic solvent at a temperature greater than about 130° C.

Embodiment A77. The method of Embodiment A51 wherein when Y is Cl then reagent (1), reagent (2), reagent (3), reagent (4) and reagent (5) are contacted with the suitable organic solvent at a temperature greater than about 140° C.

Embodiment A78. The method of Embodiment A77 wherein when Y is Cl then reagent (1), reagent (2), reagent (3), reagent (4) and reagent (5) are contacted with the suitable organic solvent at a temperature greater than about 155° C.

Embodiment A79. The method of Embodiment A1 wherein Y is Br and the compound of Formula 1 is prepared as a solid, comprising contacting reagent (1) with a suitable organic solvent to form a mixture, and then sequentially adding reagent (2), reagent (3), reagent (4) and reagent (5) to the mixture, maintaining the temperature of the mixture between about 120 and 160° C. for about 2 to about 24 h, cooling the mixture to between about 0 and 50° C., adding water to the mixture, optionally stirring for about 15 to about 30 minutes, and then recovering a compound of Formula 1 as a solid from the mixture.

Embodiment A80. The method of Embodiment A1 wherein Y is Cl and the compound of Formula 1 is prepared as a solid, comprising contacting reagent (1) with a suitable organic solvent to form a mixture, and then sequentially adding reagent (2), reagent (3), reagent (4) and reagent (5) to the mixture, maintaining the temperature of the mixture between about 160 and 200° C. for about 2 to about 24 h, cooling the mixture to about 0 to 50° C., adding water to the mixture, optionally stirring for about 15 to about 30 minutes, and then recovering a compound of Formula 1 as a solid from the mixture.

Embodiment A81. The method of any one of Embodiments A79 and A80 wherein the compound of Formula 1 is 2-amino-5-cyano-N,3-dimethylbenzamide.

Embodiment A82. The method of Embodiment A1 wherein $R^1$ is $NHR^3$ and Y is Br further comprising preparing reagent (1) using a method comprising introducing (a) a gas containing bromine into (b) a liquid containing a compound of Formula 4.

Embodiment B1. The method described in the Summary of the Invention for preparing a compound of Formula 2 comprising introducing reagent (a) (i.e. a gas containing bromine) into reagent (b) (i.e. a liquid containing a compound of Formula 4).

Embodiment B2. The method of Embodiment B1 wherein reagent (a) and reagent (b) are contacted in the presence of a base.

Embodiment B3. The method of Embodiment B2 wherein the base comprises one or more compounds selected from the group consisting of alkali metal hydroxides, carbonates and bicarbonates (e.g., sodium hydroxide, potassium hydroxide, sodium carbonate, potassium carbonate, sodium bicarbonate and potassium bicarbonate), organic bases (e.g., triethylamine, tert-butylamine) and alkali metal salts of carboxylic acids (e.g., sodium acetate, potassium acetate, sodium propionate and potassium propionate).

Embodiment B4. The method of Embodiment B3 wherein the base comprises sodium hydroxide or sodium acetate.

Embodiment B5. The method of Embodiment B1 wherein $R^3$ is $C_1$-$C_4$ alkyl, cyclopropyl, cyclopropylcyclopropyl, cyclopropylmethyl or methylcyclopropyl.

Embodiment B6. The method of Embodiment B5 wherein $R^3$ is $C_1$-$C_4$ alkyl or cyclopropylmethyl.

Embodiment B7. The method of Embodiment B6 wherein $R^3$ is methyl.

Embodiment B8. The method of Embodiment B1 wherein reagent (b) comprises one or more organic solvents selected from the group consisting of aliphatic carboxylic acids (e.g., acetic acid, propionic acid and butyric acid) and amides (e.g., N,N-dimethylformamide and N,N-dimethylacetamide).

Embodiment B9. The method of Embodiment B8 wherein reagent (b) comprises acetic acid.

Embodiment B10. The method of any one of Embodiments B8 and B9 wherein reagent (b) comprises water.

Embodiment B11. The method of Embodiment B8 wherein the total volume of the one or more solvents comprising reagent (b) relative to the weight of the compound of Formula 4 is at least about 2 mL/g.

Embodiment B12. The method of Embodiment B11 wherein the total volume of the one or more solvents comprising reagent (b) relative to the weight of the compound of Formula 4 is at least about 3 mL/g.

Embodiment B13. The method of Embodiment B12 wherein the total volume of the one or more solvents comprising reagent (b) relative to the weight of the compound of Formula 4 is at least about 5 mL/g.

Embodiment B14. The method of Embodiment B8 wherein the total volume of the one or more solvents comprising reagent (b) relative to the weight of the compound of Formula 4 is not larger than about 10 mL/g.

Embodiment B15. The method of Embodiment B14 wherein the total volume of the one or more solvents comprising reagent (b) relative to the weight of the compound of Formula 4 is not larger than about 6 mL/g.

Embodiment B16. The method of Embodiment B1 wherein the mole ratio of bromine in reagent (a) to the compound of Formula 4 is at least about 0.95.

Embodiment B17. The method of Embodiment B16 wherein the mole ratio of bromine in reagent (a) to the compound of Formula 4 is at least about 1.

Embodiment B18. The method of Embodiment B1 wherein the mole ratio of bromine in reagent (a) to the compound of Formula 4 is not larger than about 1.05.

Embodiment B19. The method of Embodiment B18 wherein the mole ratio of bromine in reagent (a) to the compound of Formula 4 is not larger than about 1.1.

Embodiment B20. The method of Embodiment B1 wherein reagent (a) and reagent (b) are contacted at a temperature not greater than about 90° C.

Embodiment B21. The method of Embodiment B20 wherein reagent (a) and reagent (b) are contacted at a temperature not greater than about 70° C.

Embodiment B22. The method of Embodiment B1 wherein reagent (a) and reagent (b) are contacted at a temperature greater than about 25° C.

Embodiment B23. The method of Embodiment B22 wherein reagent (a) and reagent (b) are contacted at a temperature greater than about 45° C.

Embodiment B24. The method of Embodiment B23 wherein reagent (a) and reagent (b) are contacted at a temperature greater than about 60° C.

Embodiment C1. The method described in the Summary of the Invention for preparing, a compound of Formula 5 using a compound of Formula 1 prepared from a compound of Formula 2.

Embodiment C2. The method of Embodiment C1 wherein Z is N.

Embodiment C3. The method of Embodiment C1 wherein $R^3$ is H, $C_1$-$C_4$ alkyl, cyclopropyl, cyclopropylcyclopropyl, cyclopropylmethyl or methylcyclopropyl.

Embodiment C4. The method of Embodiment C3 wherein $R^3$ is $C_1$-$C_4$ alkyl or cyclopropylmethyl.

Embodiment C5. The method of Embodiment C4 wherein $R^3$ is methyl.

Embodiment C6. The method of Embodiment C1 wherein $R^2$ is methyl.

Embodiment C7. The method of Embodiment C1 wherein $R^{14}$ is Br.

Embodiment C8. The method of Embodiment C1 wherein $R^{15}$ is Cl.

Embodiment C9. The method of Embodiment C1 wherein $R^{16}$ is H.

Embodiment C10. The method of Embodiment C1 wherein Z is CH.

Embodiment D1. The method of Embodiment A1 wherein reagent (2) comprises a compound of Formula 6

$$M^1CN \qquad 6$$

wherein $M^1$ is an alkali metal;

Embodiment D2. The method of Embodiment D1 wherein reagent (2) is a compound of Formula 6.

Embodiment D3. The method of Embodiment D1 or D2 wherein $M^1$ is selected from the group consisting of sodium and potassium.

Embodiment D4. The method of Embodiment D3 wherein $M^1$ is sodium.

Embodiment D5. The method of Embodiment D1 or D2 wherein the mole ratio of reagent (2) to reagent (1) is at least about 1.

Embodiment D6. The method of Embodiment D5 wherein the mole ratio of reagent (2) to reagent (1) is at least about 1.15.

Embodiment D7. The method of Embodiment D1 or D2 wherein the mole ratio of reagent (2) to reagent (1) is not larger than about 1.5.

Embodiment D8. The method of Embodiment D7 wherein the mole ratio of reagent (2) to reagent (1) is not larger than about 1.25.

Embodiments of this invention can be combined in any manner. Of note is the method of any one of Embodiments A1-A37, A40-A46, A49-A56, A58-A68, A71-A79, A81-A82, B1-B24, C1-C10 and D1-D8 wherein Y is Br. Also of note is the method of any one of Embodiments A1-A5, A7-A33, A35-A40, A42-A43, A45-A48, A50-A55, A57-A72, A77-A78, A80-A81, C1-C10 and D1-D8 wherein Y is Cl.

In the following Schemes 1-9 the definitions of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, X, Y, Z and n in the compounds of Formulae 1 through 12 are as defined above in the Summary of the Invention and description of Embodiments unless otherwise indicated. Formulae 1a, 1b and 1c are subsets of Formula 1. Formulae 2a and 2b are subsets of Formula 2.

As shown in Scheme 1, in a method of the present invention a compound of Formula 1 is prepared by contacting a compound of Formula 2 with a metal cyanide reagent, a copper(I) salt reagent, an iodide salt reagent and at least one compound of Formula 3.

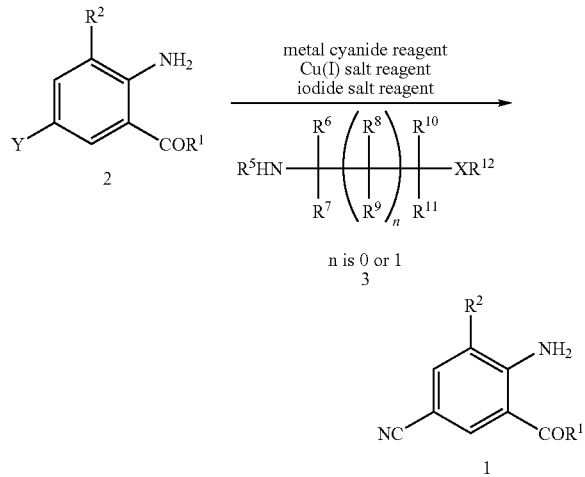

In the present method the metal cyanide reagent particularly comprises at least one compound selected from the group consisting of alkali metal cyanides or alkali metal hexacyanoferrates(II). Suitable alkali metal cyanides include compounds of the formula $M^1CN$ (i.e. Formula 6, as described above in the Embodiments), wherein $M^1$ is an alkali metal such as sodium or potassium. Suitable alkali metal hexacyanoferrates(II) include, for example, potassium hexacyanoferrate(II) and sodium hexacyanoferrate(II); both of which are commercially available at low cost, are non-toxic, easy to handle, and have six cyanide ions available for transfer to compounds of Formula 2. Highest yields of Formula 1 compounds are usually achieved when using a metal cyanide reagent comprising sodium cyanide. Typically the cyanide equivalent ratio of the metal cyanide reagent relative to the compound of Formula 2 is from about 1 to about 1.5, and more preferably from about 1.15 to about 1.25. When using alkali metal cyanides, reducing the particle size of the alkali metal cyanides prior to use can facilitate optimal yields of Formula 1 compounds. Grinding or milling alkali metal cyanides before use can provide smaller particle size material.

In the method of Scheme 1, copper(I) is believed to act as a source of a chemical species which catalyzes the conversion of Formula 2 compounds to Formula 1. Suitable copper(I) salt reagents comprise one or more compounds selected from the group consisting of copper(I) salts such as copper(I) iodide, copper(I) bromide, copper(I) chloride, copper(I) cyanide and copper(I) triflate ($CuOSO_2CF_3$). The mole ratio of the copper (I) salt reagent (based on Cu(I)) to the compound of Formula 2 is from about 0.01 to about 1, and preferably from about 0.1 to about 0.99, and more preferably from about 0.1 to about 0.4. When Y is Br, most preferred are mole ratios from about 0.15 to about 0.2 of the copper(I) salt to the compound of Formula 2. When Y is Cl, most preferred are mole ratios from about 0.3 to about 0.4 of the copper(I) salt to the compound of Formula 2.

Without being bound by any particular theory, it is believed under the conditions of the present method a 5-(bromo or chloro)benzoic acid or derivative of Formula 2 is converted to the corresponding 5-iodobenzoic acid or derivative in the presence of an iodide salt. Suitable iodide salt reagents comprise one or more compounds selected from the group consisting of quaternary ammonium, alkali and alkaline earth metal iodide salts such as copper(I) iodide, sodium iodide, potassium iodide, zinc iodide, lithium iodide, calcium iodide, tetrabutylammonium iodide and tetramethylammonium iodide. The mole ratio of the iodide salt to the compound of Formula 2 is from about 0.001 to about 1, and preferably from about 0.05 to about 0.4, and more preferably from about 0.1 to about 0.4.

In the method of Scheme 1 highest yields of Formula 1 compounds with optimal reaction rates are often obtained when copper(I) iodide is used as the source of the copper(I) salt reagent and the iodide salt reagent. When copper(I) iodide is used in the present method typically the mole ratio is from about 0.1 to about 0.4 relative to the compound of Formula 2. In some cases it may be beneficial to use copper(I) iodide in combination with another iodide salt reagent, such as sodium iodide, potassium iodide, zinc iodide, tetrabutylammonium iodide or tetramethylammonium iodide. The usefulness of copper(I) iodide plus another iodide salt reagent depends on the specific reaction conditions and substrate. Typically optimal yields of Formula 1 compounds can be obtained from the present process simply by using copper(I) iodide as the only source of iodide salt reagent.

Compounds of Formula 3 are bidentate chelating ligands comprising nitrogen and/or nitrogen-oxygen binding sites. These ligands have been found to accelerate the rate of conversion of compounds of Formula 2 to Formula 1. Without being bound by any particular theory, the ligands are thought to facilitate the reaction by increasing the solubility and/or reactivity of the copper(I) catalyst via the formation a copper-ligand complex. Compounds of Formula 3 wherein X is $NR^{13}$ are preferred such as, but not limited to, aliphatic diamines. In the method of Scheme 1 typically the highest yields of Formula 1 compounds and the most favorable reaction rates are achieved with the use of one or more of the following commercially available ligands: N,N'-dimethylethylenediamine, N,N'-dimethyl-1,3-propanediamine or 2,2-dimethyl-1,3-propanediamine. The mole ratio of Formula 3 compounds to the copper(I) salt reagent is typically from about 1 to about 10. As mole ratios greater than 1 can often accelerate the reaction while ratios above 6 generally offer little additional benefit while increasing cost, the ratio is preferably from about 4 to about 6. Besides facilitating the reaction, using mole ratios of compounds of Formula 3 to the copper(I) salt reagent of greater than 1 has been discovered to reduce the level of residual copper impurities remaining in the desired product after simple purification such as dilution with water, filtration, washing with water and optionally an organic solvent. When N,N'-dimethylethylenediamine is used as the ligand, typically mole ratios of at least about 5 relative to the copper(I) salt reagent are effective in minimizing the presence of residual copper impurities in the Formula 1 products.

The reaction of Scheme 1 is typically conducted in a suitable organic solvent. A variety of solvents can be used to form the suitable solvent for this method. Typically, the method is most satisfactorily conducted using solvents in which compounds of Formula 2 are preferably completely or at least substantially soluble and the metal cyanide reagent has a low solubility in the volume of solvents used and at ordinary ambient temperatures. Examples of suitable solvents include halogenated and nonhalogenated aliphatic and aromatic hydrocarbons such as heptane, xylenes, toluene, chlorobenzene, 1,2,4-trimethylbenzene, 1,3,5-trimethylbenzene, ethylbenzene, (1-methylethyl)benzene (also known as cumene) and $C_1$-$C_3$ alkyl-substituted naphthalenes (e.g., 1-methylnaphthalene, 2-methylnaphthalene, 1,5-dimethylnaphthalene, 2,6-dimethylnaphthalene and 1,3-dimethylnaphthalene). Of particular note as the solvent is 1,2-dimethylbenzene (o-xylene), 1,3-dimethylbenzene (m-xylene), 1,4-dimethylbenzene (p-xylene) or an isomeric mixture thereof, which is commonly known as xylenes. When Y is Br, the reaction has been discovered to rapidly proceed in xylene solvents at temperatures near the normal boiling points of the solvents to often provide products in superior yield and/or purity. Although a single xylene isomer (i.e. o-xylene, m-xylene or p-xylene) can be used as the solvent, use of the isomeric mixture of xylenes is commercially preferable as it provides equally good results at lower cost. When Y is Cl, solvents that allow for reaction temperatures between about 160 and 200° C. are preferred. This can be accomplished by using a solvent with a boiling point within or above this range or by operating at elevated pressure with a lower boiling solvent such as xylenes. When Y is Cl, 1-methylnaphthalene is a particularly useful solvent. The volume of the organic solvent relative to the weight of the compound of Formula 2 is typically between about 2 mL/g and about 10 mL/g. Amounts of solvent greater than 2 mL/g can facilitate stirring the reaction mixture, but larger amounts of solvent can slow the reaction as well as increase cost, so preferably the volume of solvent to the weight of the compound Formula 2 is between about 3 mL/g and about 6 mL/g.

In the present method, the order in which the reactants are combined is not critical to the outcome of the reaction. However, for preparing compounds of Formula 1 the most preferred order of combination has been found to comprise combining the compound of Formula 2 with the suitable organic solvent to form a mixture, and then sequentially adding the metal cyanide reagent, the copper(I) salt reagent, the iodide salt reagent and the compound or compounds of Formula 3 to the mixture. For preparing compounds of Formula 1, it has been found advantageous to purge the reaction mixture with an inert gas such as nitrogen or argon, particularly prior to the addition of the metal cyanide reagent. Therefore an embodiment of note of the present method comprises the steps of combining the compound of Formula 2 with the suitable organic solvent to form a mixture, adding the metal cyanide reagent to the mixture, followed by the copper(I) salt reagent, the iodide salt reagent, purging with an inert gas, and then adding the compound or compounds of Formula 3.

The present method is typically conducted at a temperature between about 115 and 200° C. and more typically between about 120 and 190° C. When Y is Br, temperatures between about 120 and 160° C. often achieve the highest product yield and purity with the most favorable reaction rates; for example, in most cases compounds of Formula 1 are obtained in greater than 95% yields in about 3 to about 4 h. When Y is Cl, temperatures between about 160 and 200° C., and more typically between about 170 and 180° C., often provide favorable reaction rates.

The product of Formula 1 can be isolated by standard techniques known in the art, including filtration, extraction, evaporation and crystallization. For example, the reaction medium can be diluted with about 2 to 8 parts by weight of water relative to the compound of Formula 2 to dissolve inorganic salts that are present in the reaction medium. As the compounds of Formula 1 are typically solids at ambient temperature and generally sparingly soluble in the reaction solvent, they are most easily isolated by filtration, followed by washing with water and optionally an organic solvent, such as the reaction solvent (e.g., xylenes). If the compounds of Formula 1 are soluble in the reaction solvent, they are most conveniently isolated by diluting the reaction medium with water to dissolve inorganic salts, then separating the organic phase, optionally followed by washing with water, to remove residual amounts of salts and/or metal cyanides, and then removal of the solvent by distillation or evaporation at reduced pressure. In some cases it may be advantageous to add a water-soluble copper chelating agent such as 2,2'-thiodiethanol prior to isolation of compounds of Formula 1 to optimize the removal of copper. Compounds of Formula 1 can be further purified by recrystallization from an appropriate organic solvent. Examples of appropriate solvents include alcohols, such as methanol. The method of Scheme 1 is illustrated in Examples 2-5 below.

The features of the present method provide an efficient means to produce 3-substituted 2-amino-5-cyanobenzoic acid derivatives of Formula 1 in typically high yields (>95%), in 3 to 6 h, while using inexpensive reagents. Of particular note is that the present method can be used to provide remarkably high yields of the compounds of Formula 1 in excellent purity even though these compounds as well as the starting compounds of Formula 2 contain amino substituents and in some cases amide substituents that can potentially participate in side reactions.

As shown in Scheme 2, starting compounds of Formula 2 can be prepared by halogenation of a compound of Formula 7 using a variety of reagents known in the literature including bromine, chlorine, sulfuryl chloride, N-chlorosuccinimide (NCS), N-bromosuccinimide (NBS) and halogenating reagents such as mixtures comprising hydrogen peroxide and a hydrogen halide. For leading references describing these methods, see PCT Patent Publications WO 1998/16503 (Scheme 4 and Example 132), WO 2006/068669 (Scheme 11), WO 2003/015519 (Scheme 4 and Example 1, Step A) and WO 2006/062978 (Scheme 15; Example 4, Step B and Example 5, Step B).

Scheme 2

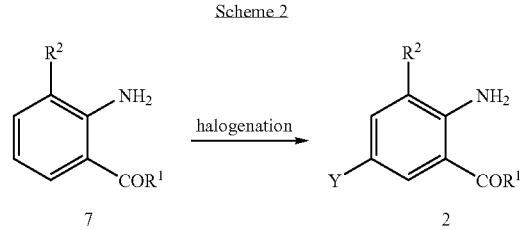

Compounds of Formula 2a (Formula 2 wherein $R^1$ is $NHR^3$) can also be prepared by contacting an isatoic anhydride of Formula 8 with an alkyl amine of Formula 9 in the presence of a carboxylic acid as illustrated in Scheme 3.

Scheme 3

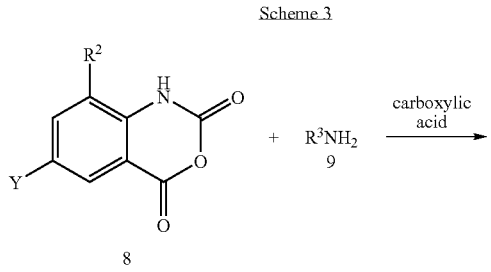

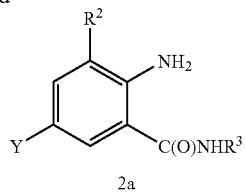

2a

As amines such as the compound of Formula 9 are bases, in the absence of the carboxylic acid the mixture of the compounds of Formulae 8 and 9 would be basic (e.g., effective pH>7). The carboxylic acid acts as a buffer to reduce the effective pH of the reaction mixture. A wide variety of carboxylic acids are useful, as the only requirement is for at least one carboxylic acid group to impart acidity. Other functional groups can be present, and more than one carboxylic acid group can be present on the carboxylic acid molecule. Typically the carboxylic acid has an effective $pK_a$ in the range of about 2 to about 5. Carboxylic acids include, for example, formic acid, propionic acid, chloroacetic acid, benzoic acid, phthalic acid, maleic acid, tartaric acid and citric acid. For reason of cost, inexpensive carboxylic acids such as formic acid, acetic acid, propionic acid and benzoic acid are preferred. Acetic acid, which is commercially available at low cost in its anhydrous form (known as "glacial acetic acid"), is particularly preferred.

The combination of the carboxylic acid with the basic amine of Formula 9 forms an amine salt of the carboxylic acid. This amine salt can be preformed before addition of the isatoic anhydride compound of Formula 8, or the amine salt can be generated in situ by metering the amine of Formula 9 into a mixture of the compound of Formula 8 and the carboxylic acid. For either mode of addition, maintaining the effective pH of the mixture during the reaction between about 3 and about 7 is generally best.

As the effective pH of the mixture results from the buffering effect of the carboxylic acid in combination with the amine of Formula 9, the effective pH can be adjusted according to the effective $pK_a$ of the carboxylic acid by adjusting the molar ratio of carboxylic acid to amine of Formula 9. Typically the molar amounts of the amine of Formula 9 to carboxylic acid are in the range from about 0.8 to about 3. More particularly, when the mode of combination involves metering the amine of Formula 9 into a mixture of the isatoic anhydride compound of Formula 8 and carboxylic acid, the molar ratio of Formula 9 amine to carboxylic acid is preferably from about 0.95 to about 3. When the mode of combination involves forming the amine salt before addition of the compound of Formula 8 the molar ratio of Formula 9 amine to carboxylic acid is preferably from about 0.8 to about 1.05; as long as a nearly equimolar ratio (e.g., about 0.95 to about 1.05) of Formula 9 amine to carboxylic acid is used, the amine salt thus formed is typically used in a ratio of about 1.1 to about 5 molar equivalents relative to the compound of Formula 8. For optimal conversions, the molar ratio of amine of Formula 9 to isatoic anhydride compound of Formula 8 should be at least 1 although the molar ratio is preferred to be from about 1.1 to about 1.5 for reasons of efficiency and of economy, regardless of how the components are mixed. The molar amount of amine of Formula 9 relative to compound of Formula 8 can be substantially greater than 1.5, particularly when a nearly equimolar ratio (e.g., about 0.95 to about 1.05) of amine to acid is used.

Highest product yield and purity is achieved when the reaction medium is substantially anhydrous. The reaction medium is thus typically formed from substantially anhydrous compounds of Formula 8 and 9 and carboxylic acid. Preferably the reaction medium and forming materials contain about 5% or less, more preferably about 1% or less, and most preferably about 0.1% water or less (by weight). If the carboxylic acid is acetic acid, it is preferably in the form of glacial acetic acid.

The reaction of Scheme 3 is typically conducted in a liquid phase. In many cases the reaction can be carried out without solvent other than the compounds of Formulae 2a, 8 and 9 and the carboxylic acid. But a preferred procedure involves use of a solvent that can suspend and at least partially dissolve the reactants. Preferred solvents are those which are non-reactive with the reaction components and have a dielectric constant of about 5 or greater, such as alkyl nitriles, esters, ethers, or ketones. Preferably the solvent should be substantially anhydrous to facilitate achieving a substantially anhydrous reaction medium. The weight ratio of solvent to the compound of Formula 8 is typically from about 1 to about 20, and preferably about 5 for reasons of efficiency and economy.

Carbon dioxide forms as a byproduct of the reaction of Scheme 3. Most of the carbon dioxide formed evolves from the reaction medium as a gas. The addition of the compound of Formula 8 into reaction medium containing the amine of Formula 9 or the addition of the amine of Formula 9 into the reaction medium containing the compound of Formula 8 is preferably conducted at such a rate and temperature as to facilitate controlling the evolution of carbon dioxide. The temperature of the reaction medium is typically between about 5 and 75° C., more typically between about 35 and 55° C.

Compounds of Formula 2a can be isolated by standard techniques known in the art, including pH adjustment, extraction, evaporation, crystallization and chromatography. For example, the reaction medium can be diluted with about 3 to 15 parts by weight of water relative to the starting compound of Formula 8, the pH can be optionally adjusted with either acid or base to optimize the removal of either acidic or basic impurities, the water phase can be optionally separated, and most of the organic solvent can be removed by distillation or evaporation at reduced pressure. As the compounds of Formula 2a are typically crystalline solids at ambient temperature, they are generally most easily isolated by filtration, optionally followed by washing with water and then drying.

As shown in Scheme 4, isatoic anhydrides of Formula 8 can be prepared from anthranilic acids of Formula 2b (Formula 2 wherein $R^1$ is $OR^4$ and $R^4$ is H) via a cyclization reaction involving treatment of the anthranilic acids with phosgene or a phosgene equivalent such as triphosgene or an alkyl chloroformate (e.g., methyl chloroformate) in a suitable solvent such as toluene or tetrahydrofuran. The method is described in PCT Publication WO 2006/068669, including a specific example relevant to Scheme 4. For other references, see Coppola, *Synthesis* 1980, 505 and Fabis et al., *Tetrahedron*, 1998, 10789.

Scheme 4

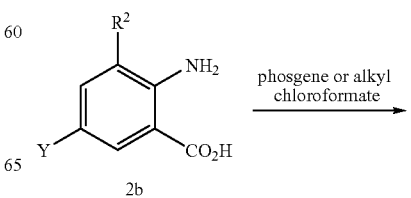

2b

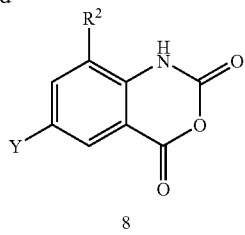

8

Schemes 2 and 3 illustrate just two methods of preparing a compound of Formula 2. In another method of the present invention a compound of Formula 2 (wherein $R^1$ is $NHR^3$ and Y is Br) can be prepared by introducing a gas containing bromine into a liquid containing a compound of Formula 4 as shown in Scheme 5.

Scheme 5

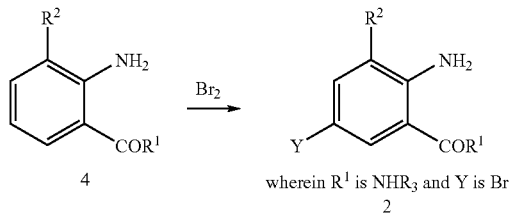

wherein $R^1$ is $NHR_3$ and Y is Br
2

In the method of Scheme 5 the liquid containing the compound of Formula 4 is a liquid phase in which the compound of Formula 4 is suspended, partially dissolved or completely dissolved, but preferably at least partially dissolved. The liquid phase can comprise organic solvents that are substantially anhydrous or, alternatively, aqueous mixtures of organic solvents. The solvents should be non-reactive with bromine at temperatures to which the reaction might be heated (e.g., about 90° C.). Organic solvents suitable for forming the liquid include, for example, aliphatic carboxylic acids such as acetic acid, propionic acid and butyric acid, and amides such as N,N-dimethylformamide and N,N-dimethylacetamide, and mixtures thereof. Acetic acid, which is commercially available at low cost is preferred. Either the anhydrous form of acetic acid (known as "glacial acetic acid") or aqueous mixtures of acetic acid can be used in the present method. The total volume of the solvents relative to the weight of the compound of Formula 4 is typically between about 2 mL/g and about 10 mL/g, and preferably between about 6 mL/g and 10 mL/g. If the liquid phase comprises water, preferably the volume of water relative to the weight of the compound of Formula 4 is between about 1.5 mL/g and about 2 mL/g.

As the method of Scheme 5 generates hydrobromic acid the reaction is preferably carried out in the presence of a base capable of binding to hydrobromic acid. Although the product of Formula 2 forms in the absence of a base, in some cases high concentrations of hydrobromic acid in the reaction mixture can inhibit bromination and lead to reduced yields. A variety of bases are suitable for reducing the presence of hydrobromic acid in the reaction mixture, including alkali metal hydroxides, carbonates and bicarbonates (e.g., sodium hydroxide, potassium hydroxide, sodium carbonate, potassium carbonate, sodium bicarbonate, potassium bicarbonate), organic bases (e.g., triethylamine, tert-butylamine) and alkali metal salts of carboxylic acids (e.g., sodium acetate, potassium acetate, sodium propionate and potassium propionate).

In the present method, the base preferably comprises one or more compounds selected from alkali metal hydroxides and alkali metal salts of carboxylic acids. Most preferably the base comprises sodium hydroxide or sodium acetate. The mole ratio of the base to the compound of Formula 4 is typically from about 1 to about 1.2, and preferably from about 1.1 to about 1.15. The base can be added in anhydrous form or as an aqueous mixture. For example, in the present method if sodium hydroxide is used it is typically added to the reaction mixture as an aqueous solution (e.g., 3 M). If an aqueous mixture of a base is used, the total amount of water added to the reaction mixture, including the water added with the base plus water added at any other time during the course of the reaction (e.g., water in aqueous organic solvents), is typically within the ranges described above.

The method of Scheme 5 is carried out using gaseous bromine. The term gaseous bromine means bromine gas, vapor or mist that can be handled like a gas. Liquid bromine is most conveniently used as the source for generating gaseous bromine, although any other source for gaseous bromine can be used. Liquid bromine is preferred (as the source of gaseous bromine) because it is readily available at relatively low cost and because it has a relatively high vapor pressure, thus allowing gas to be easily evaporated from the liquid. In the method of Scheme 5 the liquid bromine is typically at ambient temperature; however it can be heated if desired, as the vapor pressure of liquid bromine increases with increasing temperature. In either case, the gaseous bromine is best introduced below the surface of the reaction mixture to ensure high conversion of compounds of Formula 4 to compounds of Formula 2 and to minimize bromine loss. If liquid bromine is used to supply gaseous bromine, the gaseous bromine can be added to the reaction mixture by connecting the vessel containing the reaction mixture to another vessel containing the liquid bromine, then flowing an inert gas (e.g., nitrogen) below the surface of the liquid bromine, and allowing bromine vapor entrained in the nitrogen gas to flow out of the vessel containing the liquid bromine and to enter the vessel containing the reaction mixture, most preferably below the surface of the reaction mixture. The vessels containing the reaction mixture and the liquid bromine, and the equipment connected to these vessels (e.g., dip tubes) should be made of materials compatible with bromine and bromide (e.g., glass, Teflon®, and corrosion resistant metal alloys such as Hastelloy®). For optimal yields of Formula 2 compounds, the mole ratio of bromine to compounds of Formula 4 is typically from about 0.95 to about 1.1; and the concentration of bromine in the inert gas is typically in the range of about 0.005 to about 0.02 moles per liter inert gas.

In the method of Scheme 5 the preferred order of combination has been found to comprise combining the compound of Formula 4 with the one or more solvents and then adding gaseous bromine. If a base is used the compound of Formula 4 is typically first combined with the one or more solvents, and then the base is added, followed by addition of gaseous bromine.

The method of Scheme 5 is typically conducted between about 25 and 90° C. and more typically between about 45 and 60° C. To achieve reaction in this temperature range, the components are typically combined at about ambient temperature (e.g., about 15-40° C.) and then the temperature of the reaction mixture is raised to between about 45 and 60° C. More preferably, the liquid containing the compound of Formula 4 is combined with the base, the temperature is raised to between about 45 and 60° C., and then gaseous bromine is added. The reaction time is usually no more than about 2 to 3 h, but can vary depending on conditions, for example the rate at which bromine is added to the reaction mixture and the reaction temperature.

The product of Formula 2 can be isolated by standard techniques known in the art, including, filtration, extraction, evaporation and crystallization. Additionally, the pH of the reaction mixture can be adjusted prior to isolating compounds of Formula 2 by addition of a base to remove hydrobromic acid byproduct. For example, addition of about 3 to 15 parts by weight of aqueous 6 M sodium hydroxide solution relative to the starting compound of Formula 4 is often sufficient to completely neutralize the hydrobromic acid in the reaction mixture. As the compounds of Formula 2 are typically crystalline solids, they are generally most easily isolated by filtration, optionally followed by washing with water and an organic solvent, such as ethanol or methanol, and then drying.

In another aspect of the present invention compounds of the Formula 1 prepared by the method of Scheme 1 are useful as intermediates for preparing compounds of Formula 5. Compounds of Formula 5 are useful as insecticides, as described, for example in PCT Patent Publications WO 2003/015518 and WO 2006/055922.

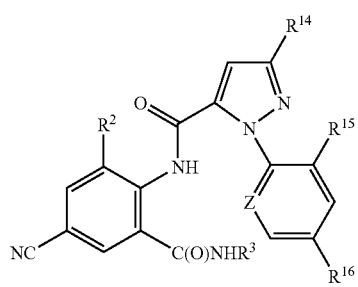

5 wherein
R$^2$ is CH$_3$ or Cl;
R$^3$ is H, C$_1$-C$_4$ alkyl, cyclopropyl, cyclopropylcyclopropyl, cyclopropylmethyl or methylcyclopropyl;
Z is CR$^{17}$ or N;
R$^{14}$ is Cl, Br, CF$_3$, OCF$_2$H or OCH$_2$CF$_3$;
R$^{15}$ is F, Cl or Br;
R$^{16}$ is H, F or Cl; and
R$^{17}$ is H, F, Cl or Br;

A variety of routes are possible for the preparation of a compound of Formula 5 from a compound of Formula 1. As outlined in Scheme 6, one such method involves the coupling of a compound of Formula 1a (Formula 1 wherein R$^1$ is OR$^4$ and R$^4$ is H) with a pyrazole-5-carboxylic acid of Formula 10, resulting in a cyanobenzoxazinone of Formula 11. Subsequent reaction of the cyanobenzoxazinone with an amine of Formula 9 provides a compound of Formula 5. Conditions for the first step involve sequential addition of methanesulfonyl chloride in the presence of a tertiary amine such as triethylamine or pyridine to a pyrazole of Formula 10, followed by the addition of a compound of Formula 1a, followed by a second addition of tertiary amine and methanesulfonyl chloride. The reaction can be run neat or in a variety of suitable solvents including tetrahydrofuran, diethyl ether, dioxane, toluene, dichloromethane or chloroform with optimum temperatures ranging from room temperature to the reflux temperature of the solvent. The second step, reaction of benzoxazinones with amines to produce anthranilamides, is well documented in the chemical literature. For a general review of benzoxazinone chemistry see Jakobsen et al., *Biorganic and Medicinal Chemistry* 2000, 8, 2095-2103 and references cited within, and G. M. Coppola, *J. Heterocyclic Chemistry* 1999, 36, 563-588. Also see PCT Patent Publication WO 2004/067528, which teaches the general method shown in Scheme 6, including experimental examples relevant to Scheme 6.

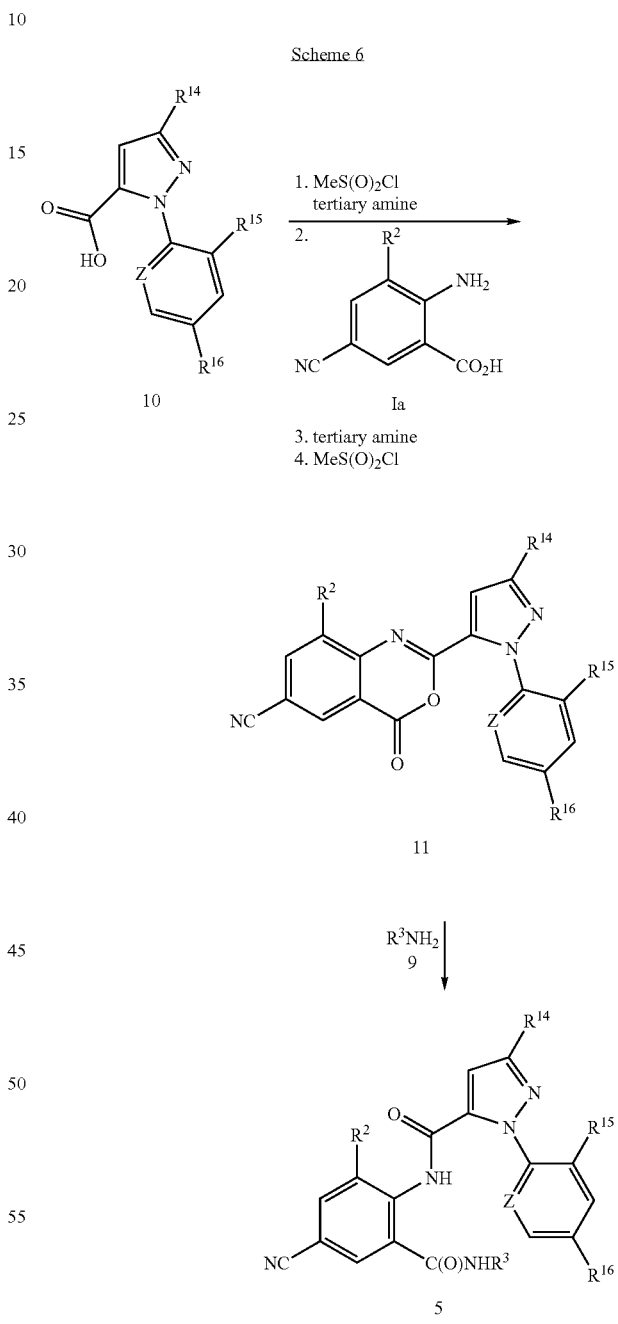

Another method of preparing compounds of Formula 5 is shown in Scheme 7. In this method a compound of Formula 5 is prepared by combining a compound of Formula 1b (Formula 1 wherein R$^1$ is NHR$^3$), a pyrazole of Formula 10 and sulfonyl chloride according to the general method taught in PCT Patent Publication WO 2006/062978, which is hereby incorporated herein in its entirety by reference.

Scheme 7

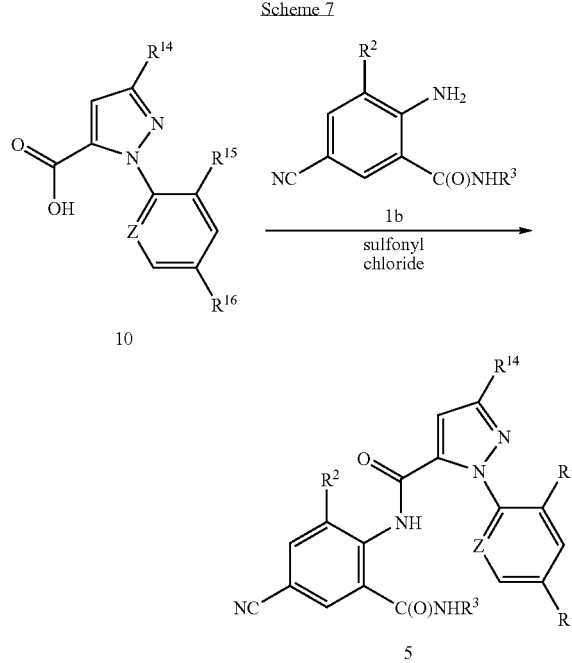

As described in WO 2006/062978 a variety of reaction conditions are possible for this method. Typically a sulfonyl chloride is added to a mixture of the compounds of Formulae 1b and 10 in the presence of a solvent and a base. Sulfonyl chlorides are generally of the formula $RS(O)_2Cl$ wherein R is a carbon-based radical. Typically for this method R is $C_1$-$C_4$ alkyl, $C_1$-$C_2$ haloalkyl, or phenyl optionally substituted with 1-3 substituents independently selected from the group consisting of halogen, $C_1$-$C_3$ alkyl and nitro. Commercially available sulfonyl chlorides include methanesulfonyl chloride (R is $CH_3$), propanesulfonyl chloride (R is $(CH_2)_2CH_3$), benzenesulfonyl chloride (R is phenyl), and p-toluenesulfonyl chloride (R is 4-methylphenyl). Methanesulfonyl chloride is of note for reasons of lower cost, ease of addition and/or less waste. At least one molar equivalent of the sulfonyl chloride per mole of the compound of Formula 10 is stoichiometrically needed for complete conversion. Typically the mole ratio of sulfonyl chloride to the compound of Formula 10 is no more than about 2.5, more typically no more than about 1.4.

Compound of Formula 5 is formed when the starting compounds of Formulae 1b, 10 and the sulfonyl chloride are contacted with each other in a combined liquid phase, in which each is at least partially soluble. Particularly as the starting materials of Formulae 1b and 10 are typically solids at ordinary ambient temperatures, the method is most satisfactorily conducted using a solvent in which the starting compounds have significant solubility. Thus typically the method is conducted in a liquid phase comprising a solvent. In some cases the carboxylic acid of Formula 10 may have only slight solubility but its salt with added base may have more solubility in the solvent. Suitable solvents for this method include nitriles such as acetonitrile and propionitrile; esters such as methyl acetate, ethyl acetate, and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF), and p-dioxane; aromatic hydrocarbons such as benzene, toluene, chlorobenzene, and dichlorobenzene; tertiary amines such as trialkylamines, dialkylanilines, and optionally substituted pyridines; and mixtures of the foregoing. Solvents of note include acetonitrile, propionitrile, ethyl acetate, acetone, MEK, dichloromethane, methyl tert-butyl ether, THF, p-dioxane, toluene, and chlorobenzene. Of particular note as the solvent is acetonitrile, as it often provides products in superior yield and/or purity.

As the reaction of the present method generates hydrogen chloride as a byproduct, which would otherwise bind to basic centers on the compounds of Formulae 1b, 5 and 10, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 10 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as the solvent the nominal mole ratio of the base to the sulfonyl chloride is typically from about 2.0 to 2.2, and is preferably from about 2.1 to 2.2. Preferred bases are tertiary amines, including substituted pyridines. More preferred bases include 2-picoline, 3-picoline, 2,6-lutidine, and pyridine. Of particular note as the base is 3-picoline, as its salts with carboxylic acids of Formula 10 are often highly soluble in solvents such as acetonitrile.

A variety of methods known to those skilled in the art can be used to isolate compounds of Formula 5, including crystallization, filtration and extraction. As disclosed in WO 2006/062978, in some cases under the coupling reaction conditions of Scheme 7 the compounds of Formula 5, can partial cyclize to form iminobenzoxazine derivatives of Formula 12, as shown below in Scheme 8.

Scheme 8

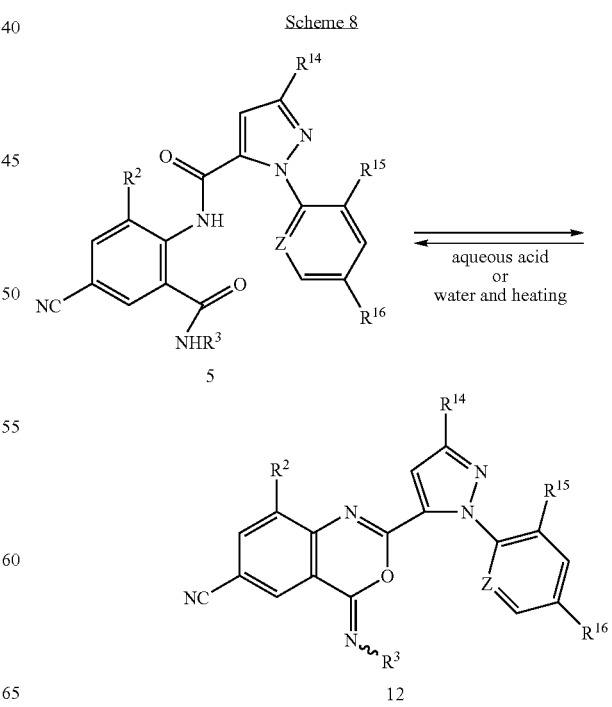

As discussed in WO 2006/062978, in these cases it is often advantageous to convert the iminobenzoxazine compounds of Formula 12 back to the amides of Formula 5 prior to isolation. This conversion can be accomplished by treatment of the reaction mixture with an aqueous acid solution (e.g., aqueous hydrochloric acid); or by isolating the mixture of Formula 12 and Formula 5 compounds, and then treating the mixture with an aqueous acid solution, optionally in the presence of a suitable organic solvent (e.g., acetonitrile). WO 2006/062978 discloses specific examples relevant to the method of Scheme 7, including examples illustrating treatment of the reaction mixture with an aqueous acid solution prior to isolating compounds of Formula 5. Example 6 below also illustrates the method of Scheme 7 including treatment of the reaction mixture with water and hydrochloric acid prior to isolating the Formula 5 product.

Alternatively, compounds of Formula 12 can be converted back to compounds of Formula 5 prior to isolation by contacting the reaction mixture with water and heating. Typically, the conversion of Formula 12 compounds to Formula 5 compounds can be achieved by adding between about 2 to 6 parts by weight of water relative to the weight of the starting compound of Formula 1 and then heating to between about 45 and 65° C. The conversion of the compound of Formula 12 to the compound of Formula 5 is usually complete in 1 h or less. Reference Example 1 below illustrates the method of Scheme 7 including the treatment of the reaction mixture with water and heating prior to isolating the compound of Formula 5.

Pyrazole-5-carboxylic acids of Formula 10 can be prepared from 5-oxo-3-pyrazolidinecarboxylates by treatment with a halogenating reagent to give 3-halo-4,5-dihydro-1H-pyrazole-5-carboxylates, which can subsequently be treated with an oxidizing agent to provide esters of the acids of Formula 10. The esters can then be converted to the acids (i.e. Formula 10). Halogenating agents that can be used include, for example, phosphorous oxyhalides, phosphorous trihalides, phosphorous pentahalides, thionyl chloride, dihalotrialkylphosphoranes, dihalodiphenylphosphoranes, oxalyl chloride and phosgene. The oxidizing agents can be, for example, hydrogen peroxide, organic peroxides, potassium persulfate, sodium persulfate, ammonium persulfate, potassium monopersulfate (e.g., Oxone®) or potassium permanganate. See PCT Publications WO 2003/016283, WO 2004/087689 and WO 2004/011453 for a description of the halogenation and oxidation methods, and a procedure for preparing the starting 5-oxo-3-pyrazolidinecarboxylates. To convert the esters to carboxylic acids a variety of methods reported in the chemical literature can be used, including nucleophilic cleavage tinder anhydrous conditions or hydrolysis involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods). Base-catalyzed hydrolytic methods are preferred to prepare the carboxylic acids of Formula 10 from the corresponding esters. Suitable bases include alkali metal (such as lithium, sodium, or potassium) hydroxides. For example, the esters can be dissolved in a mixture of water and alcohol such as methanol. Upon treatment with sodium hydroxide or potassium hydroxide, the ester saponifies to provide the sodium or potassium salt of the carboxylic acid. Acidification with a strong acid, such as hydrochloric acid or sulfuric acid, gives the carboxylic acid. PCT Publication WO 2003/016283 provides a relevant experimental example illustrating the base-catalyzed hydrolysis method for the conversion of an ester to an acid.

Alternatively, pyrazole-5-carboxylic acids of Formula 10 can be prepared from 4,5-dihydro-5-hydroxy-1H-pyrazole-5-carboxylates via an acid-catalyzed dehydration reaction to give esters, which can then be converted to the acids of Formula 10. Typical reaction conditions involve treatment of 4,5-dihydro-5-hydroxy-1H-pyrazole-5-carboxylates with an acid, for example, sulfuric acid, in an organic solvent, such as acetic acid, at temperatures between 0 and 100° C. The method is described PCT Publication WO 2003/016282. Conversion of the esters to acids can be done using the methods described above. Also, WO 2003/016282 provides a relevant experimental example for the conversion of an ester to an acid.

Anthranilic amides of Formula 1b can also be prepared from the anthranilic acid or ester derivatives of Formula 1c (Formula 1 wherein $R^1$ is $OR^4$ and $R^4$ is H or $C_1$-$C_4$ alkyl) as shown below in Scheme 9. Forming amides from carboxylic acids typically involves addition of a coupling agent (e.g., silicon tetrachloride, or alternatively dicyclohexylcarbodiimide or 1-ethyl-3-(3-dimethylaminopropyl)carbodiimide often in the presence of 1-hydroxybenzotriazole). Preparation of anthranilic amides from anthranilic acids is disclosed in M. J. Kornet, *Journal of Heterocyclic Chemistry* 1992, 29(1), 103-5; PCT Publication WO 2001/66519-A2; T. Asano et al., *Bioorganic & Medicinal Chemistry Letters* 2004, 14(9), 2299-2302; H. L. Birch et al., *Bioorganic& Medicinal Chemistry Letters* 2005, 15(23), 5335-5339; and D. Kim et al., *Bioorganic& Medicinal Chemistry Letters* 2005, 15(8), 2129-2134. T. Asano et al. also reports preparation of an anthranilic amide from an anthranilic acid through an N-protected aniline intermediate or through a 4H-3,1-benzoxazine-2,4(1H)-dione (isatoic anhydride) intermediate. Forming amides from esters often involves heating the ester with the appropriate amine in a polar solvent such as ethylene glycol. A procedure useful for conversion of anthranilic esters to anthranilic amides is described in PCT Publication WO 2006/062978. Also, E. B. Skibo et al., *Journal of Medicinal Chemistry* 2002, 45(25), 5543-5555 discloses preparation of an anthranilic amide from the corresponding anthranilic ester and amine using sodium cyanide catalyst.

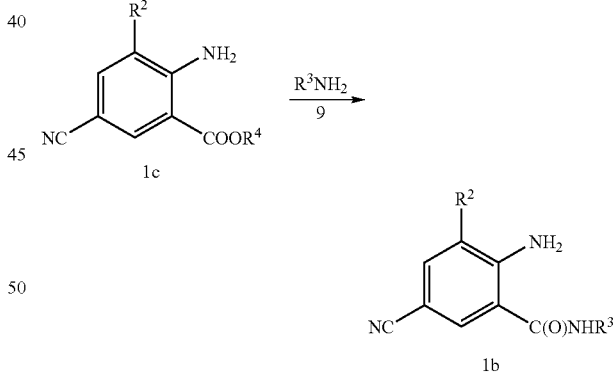

Scheme 9

The methods of Schemes 6 and 7 are illustrative of just two of many methods for converting a compound of Formula 1 to the carboxamide compound of Formula 5. A wide variety of general methods known in the art for preparing carboxamides from carboxylic acids and amines. For a general review, see M. North, *Contemporary Org. Synth.* 1995, 2, 269-287. Particular methods include contacting a compound of Formula 1b with a compound of Formula 10 in the presence of a dehydrating coupling agent such as 1,1'-carbonyldiimidazole, bis(2-oxo-3-oxazolidinyl)phosphinic chloride or benzotriazol-1-yloxytris(dimethylamino)phosphonium hexafluorophosphate, or a polymer-bound analogous reagent such as polymer-bound dicyclohexylcarbodiimide, typically in an inert solvent such as dichloromethane or N,N-dimethylformamide, as is generally disclosed in PCT Patent Publication WO 2003/15518. Also disclosed in WO 2003/15518 is a method of preparing an acyl chloride counterpart of the compound of Formula 10, such as by contact with thionyl chloride or oxalyl chloride in the presence of a catalytic amount of N,N-dimethylformamide, and then contacting the derived acyl chloride with the compound of Formula 1b in the presence of an acid scavenger, such as an amine base (e.g., triethylamine, N,N-diisopropylethylamine, pyridine, and polymer-supported analogs) or a hydroxide or carbonate (e.g., NaOH, KOH, $Na_2CO_3$, $K_2CO_3$), typically in an inert solvent such as tetrahydrofuran, 1,4-dioxane, ethyl ether or dichloromethane. The product compounds of Formula 5 can be isolated from the reaction mixtures by methods known to those skilled in the art, including crystallization, filtration, and extraction.

Without further elaboration, it is believed that one skilled in the art using the preceding description can utilize the present invention to its fullest extent. The following Examples are, therefore, to be construed as merely illustrative, and not limiting of the disclosure in any way whatsoever. The following Examples illustrate synthesis procedures, and the starting material of each Example may not have necessarily been prepared by a particular preparative run whose procedure is described in other Examples. $^1$H NMR spectra are reported in ppm downfield from tetramethylsilane; s is singlet, d is doublet, m is multiplet, br s is broad singlet, and br d means broad doublet.

EXAMPLE 1

Preparation of
2-amino-5-bromo-N,3-dimethylbenzamide (a Compound of Formula 2)

A 1000-mL flask equipped with a mechanical stirrer, thermocouple, condenser and Teflon® fluoropolymer tubing (¹⁄₁₆" (0.16 cm) I.D.×⅛" (0.32 cm) O.D.) (positioned such that the end of the tubing was submerged below the surface of the reaction mixture) was charged with acetic acid (226 mL). A solution of aqueous sodium hydroxide (50%, 25 g) in water (85 g) was added over 15 minutes, and then 2-amino-N,3-dimethylbenzamide (50 g, 0.305 mol) (see PCT Publication WO 2006/062978 for a method of preparation) was added and the mixture was heated to 55° C. A two-necked 200-mL flask fitted on one neck with Teflon® tubing was charged with liquid bromine (50.1 g), and then the other neck was connected to the Teflon® tubing in the 1000-mL flask. Nitrogen gas was flowed through the Teflon® tubing below the surface of the liquid bromine at a rate of about 0.012 m³ (0.4 cu ft) per h for 2.5 h, during which time all of the liquid bromine evaporated and the bromine vapor entrained in the nitrogen gas flowed out of the two-necked 200-mL flask and entered the reaction mixture through the Teflon® tubing in the 1000-mL flask. The reaction temperature was held at about 55° C. during the bromine vapor addition and for 30 minutes thereafter, and then cooled to 45° C. and stirred overnight. A solution of aqueous sodium hydroxide (50%, 52 g) in water (88 mL) was added to the reaction mixture at a rate of 0.8 mL/minute. After about 10% of the total volume of the sodium hydroxide solution had been added, the addition was stopped and the reaction mixture was stirred at 45° C. for 1 h. After 1 h the remaining sodium hydroxide solution was added at rate of 0.8 mL/minute. After the addition was complete, the reaction mixture was stirred for 30 minutes at 45° C., and then cooled to 10° C. and stirred for 1 h. The mixture was filtered and the solid collected was washed with methanol (130 mL) and water (260 mL), and then dried to a constant weight in a vacuum-oven at 45° C. to give the title compound as a solid (67 g, 99.4 area % purity by HPLC, 89.7% yield) melting at 133-135° C.

$^1$H NMR (DMSO-$d_6$) δ 8.30 (m, 1H), 7.49 (d, 1H), 7.22 (d, 1H), 6.35 (br s, 2H), 2.70 (d, 3H), 2.06 (s, 3H).

EXAMPLE 2

Preparation of
2-amino-5-cyano-N,3-dimethylbenzamide (a Compound of Formula 1)

A 500-mL four-necked flask equipped with a mechanical stirrer, thermocouple, condenser and sodium hydroxide/sodium hypochlorite scrubber was charged with 2-amino-5-bromo-N,3-dimethylbenzamide (prepared by the method of Example 1) (99.1% purity, 24.1 g, 0.10 mol) and xylenes (100 g) while maintaining an atmosphere of argon through a gas inlet line connected to the condenser. The mixture was stirred at room temperature, and powdered sodium cyanide (powdered just prior to use) (6.2 g, 0.121 mol, assuming 95% purity), copper(I) iodide (2.9 g, 0.015 mol) and N,N'-dimethylethylenediamine (7.6 g, 0.085 mol) were added. Stirring was continued for an additional 15 to 20 minutes while the mixture was purged with argon, after which time the mixture was maintained under an argon atmosphere. The mixture was heated at reflux (about 140° C.), while venting through the scrubber. After 4.5 h the mixture was cooled to 25° C., water (100 mL) was added over 5 minutes, and stirring was continued for an additional 30 minutes. The mixture was filtered and the solid collected was washed with water (2×50 mL) and xylenes (50 mL), and then dried to a constant weight in a vacuum-oven at 55° C. to give the title compound (18.2 g) as an off-white solid melting at 203-204° C.

$^1$H NMR (DMSO-$d_6$) δ 8.44 (br d, 1H), 7.82 (br s, 1H), 7.44 (br s, 1H), 7.17 (br s, 2H), 2.73 (d, 3H), 2.10 (s, 3H).

EXAMPLE 3

A Second Preparation of
2-amino-5-cyano-N,3-dimethylbenzamide

A 100-mL three-necked flask equipped with a mechanical stirrer, thermometer and condenser was charged with 2-amino-5-bromo-N,3-dimethylbenzamide (prepared by the method of Example 1) (99.1% purity, 5.0 g, 0.02 mol) and chlorobenzene (20 g) while maintaining a flow of nitrogen through a gas inlet line connected to the condenser. The reaction mixture was stirred at room temperature, and powdered sodium cyanide (powdered just prior to use) (1.25 g, 0.024 mol, assuming 95% purity), copper(I) iodide (0.57 g, 0.003 mol) and N,N'-dimethylethylenediamine (1.51 g, 0.017 mol) were added. The mixture was heated at reflux (about 130° C.) for 4.5 h and then cooled to 25° C., and water (20 mL) was added over 5 minutes, and the resulting mixture was stirred for 30 minutes. The mixture was filtered, and the solid collected was washed with water (2×10 mL) and chlorobenzene (10 mL), and then dried to a constant weight in a vacuum-oven at 50° C. to give the title compound (3.6 g) as an off-white solid melting at 202-203° C.

$^1$H NMR (DMSO-$d_6$) δ 8.44 (br d, 1H), 7.82 (br s, 1H), 7.44 (br s, 1H), 7.17 (br s, 2H), 2.73 (d, 3H), 2.10 (s, 3H).

EXAMPLE 4

A Third Preparation of
2-amino-5-cyano-N,3-dimethylbenzamide

A 100-mL three-necked flask equipped with a mechanical stirrer, thermometer and condenser was charged with 2-amino-5-bromo-N,3-dimethylbenzamide (prepared by the method of Example 1) (99.1% purity, 5.0 g, 0.02 mol) and 1,3,5-trimethylbenzene (20 g) while maintaining a flow of nitrogen through a gas inlet line connected to the condenser. The reaction mixture was stirred at room temperature, and powdered sodium cyanide (powdered just prior to use) (1.25 g, 0.024 mol, assuming 95% purity), copper(I) iodide (0.57 g, 0.003 mol) and N,N'-dimethylethylenediamine (1.51 g, 0.017 mol) were added. The reaction mixture was heated to between about 138 and 140° C. for 3 h, then heated to reflux (about 155° C.), and then cooled to 23° C., and water (20 mL) was added over 5 minutes. The mixture was stirred for 30 minutes and then filtered. The solid collected was washed with water (2×10 mL), chlorobenzene (10 mL), and then dried to constant a weight in a vacuum-oven at 50° C. to give the title compound (3.3 g) as an off-white solid melting at 202-203° C.

$^1$H NMR (DMSO-$d_6$) δ 8.44 (br d, 1H), 7.82 (br s, 1H), 7.44 (br s, 1H), 7.17 (br s, 2H), 2.73 (d, 3H), 2.10 (s, 3H).

EXAMPLE 5

A Fourth Preparation of 2-amino-5-cyano-N,3-dimethylbenzamide

A 100-mL three-necked flask equipped with a mechanical stirrer, thermometer and condenser was charged with 2-amino-5-chloro-N,3-dimethylbenzamide (see PCT Publication WO 2006/062978 for a method of preparation) (4.0 g, 0.02 mol) and 1-methylnaphthalene (20 g) while maintaining a flow of nitrogen through a gas inlet line connected to the condenser. The reaction mixture was stirred at room temperature, and powdered sodium cyanide (powdered just prior to use) (1.25 g, 0.024 mol, assuming 95% purity), copper(I) iodide (1.15 g, 0.006 mol) and N,N'-dimethylethylenediamine (1.51 g, 0.017 mol) were added. The reaction mixture was heated to about 180° C. for 6 h. HPLC analysis of the reaction mixture indicated about 95% conversion of the 2-amino-5-chloro-N,3-dimethylbenzamide with 2-amino-5-cyano-N,3-dimethylbenzamide being the major product.

EXAMPLE 6

Preparation of 3-bromo-1-(3-chloro-2-pyridinyl)-N-[4-cyano-2-methyl-6-[(methylamino)carbonyl]phenyl]-1H-pyrazole-5-carboxamide (a Compound of Formula 5)

To a mixture of 3-bromo-1-(3-chloro-2-pyridinyl)-1H-pyrazole-5-carboxylic acid (see PCT Patent Publication WO 2003/015519 for a method of preparation) (97.6% purity, 3.10 g, 0.01 mol) and 2-amino-5-cyano-N,3-dimethylbenzamide (i.e. prepared by the method of Example 2) (2.00 g, 0.01 mol) in acetonitrile (24 mL) was added 3-picoline (2.92 mL, 0.03 mol). The mixture was cooled to between −5 and −10° C., and then methanesulfonyl chloride (1.08 mL, 0.014 mol) was added dropwise. The mixture was stirred for 5 minutes at −10 to −5° C., and then for 3 h at 0 to 5° C. After 3 h water (11 mL) was added dropwise to the mixture while maintaining the temperature at 0 to 5° C. After 15 minutes, concentrated hydrochloric acid (1.0 mL) was added and the mixture was stirred for 1 h at 0 to 5° C. The mixture was filtered and the solids collected were washed with acetonitrile-water (2:1 mixture, 2×2 mL) and acetonitrile (2×2 mL), and then dried under nitrogen to afford the title compound (4.78 g, 95.8% corrected yield based on assay of 95%) as an off-white solid melting at 206-208° C.

$^1$H NMR (DMSO-$d_6$) δ 10.52 (br s, 1H) 8.50 (dd, 1H), 8.36 (m, 1H), 8.17 (dd, 1H), 7.88 (d, 1H), 7.76 (d, 1H), 7.62 (m, 1H), 7.41 (s, 1H), 2.66 (d, 3H), 2.21 (s, 3H).

REFERENCE EXAMPLE 1

Preparation of 3-bromo-1-(3-chloro-2-pyridinyl)-N-[4-cyano-2-methyl-6-[(methylamino)carbonyl]phenyl]-1H-pyrazole-5-carboxamide (a Compound of Formula 5)

To a mixture of 3-bromo-1-(3-chloro-2-pyridinyl)-1H-pyrazole-5-carboxylic acid (see PCT Patent Publication WO 2003/015519 for a method of preparation) (97.4% purity, 15 g, 0.049 mol) and 2-amino-5-cyano-N,3-dimethylbenzamide (see PCT Patent Publication WO 2006/62978 for a method of preparation) (10.0 g, 0.0525 mol) in acetonitrile (80 mL) was added 3-picoline (13.9 g, 0.148 mol). The mixture was cooled to 15 to 20° C., and then methanesulfonyl chloride (8.2 g, 0.071 mol) was added dropwise. After 1 h, water (37.3 g) was added dropwise to the reaction mixture while maintaining the temperature at 15 to 20° C. The mixture was heated at 45 to 50° C. for 30 minutes, and then cooled to 15 to 25° C. for 1 h. The mixture was filtered, and the solids collected were washed with acetonitrile-water (approximately a 5:1 mixture, 2×10 mL) and acetonitrile (2×10 mL), and then dried under nitrogen to afford the title compound (24.0 g, 93.6% corrected yield based on an assay of 91.6%) as an off-white solid.

$^1$H NMR (DMSO-$d_6$) δ 10.53 (br s, 1H) 8.49 (dd, 1H), 8.36 (m, 1H), 8.16 (dd, 1H), 7.87 (d, 1H), 7.76 (d, 1H), 7.60 (m, 1H), 7.41 (s, 1H), 2.67 (d, 3H), 2.21 (s, 3H).

Table 1 illustrates the particular transformations to prepare compounds of Formula 1 according to a method of the present invention. For these transformations, the copper(I) salt reagent and the iodide salt reagent are copper(I) iodide. In Table 1 and the following tables: t means tertiary, s means secondary, n means normal, i means iso, c means cyclo, Me means methyl, Et means ethyl, Pr means propyl, and Bu means butyl. Concatenations of groups are abbreviated similarly: for example, "c-PrCH$_2$" means cyclopropylmethyl.

TABLE 1

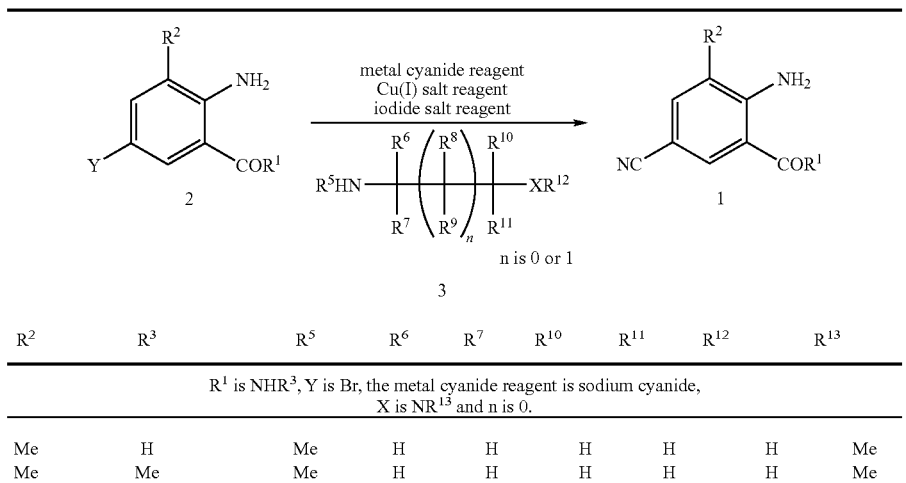

n is 0 or 1

| $R^2$ | $R^3$ | $R^5$ | $R^6$ | $R^7$ | $R^{10}$ | $R^{11}$ | $R^{12}$ | $R^{13}$ |
|---|---|---|---|---|---|---|---|---|
| $R^1$ is NHR$^3$, Y is Br, the metal cyanide reagent is sodium cyanide, X is NR$^{13}$ and n is 0. | | | | | | | | |
| Me | H | Me | H | H | H | H | H | Me |
| Me | Me | Me | H | H | H | H | H | Me |

TABLE 1-continued

| R² | R³ | R⁵ | R⁶ | R⁷ | R⁸ | R⁹ | R¹⁰ | R¹³ |
|---|---|---|---|---|---|---|---|---|
| Me | Et | Me | H | H | H | H | H | Me |
| Me | n-Pr | Me | H | H | H | H | H | Me |
| Me | i-Pr | Me | H | H | H | H | H | Me |
| Me | n-Bu | Me | H | H | H | H | H | Me |
| Me | i-Bu | Me | H | H | H | H | H | Me |
| Me | s-Bu | Me | H | H | H | H | H | Me |
| Me | t-Bu | Me | H | H | H | H | H | Me |
| Me | c-Pr | Me | H | H | H | H | H | Me |
| Me | c-PrCH₂ | Me | H | H | H | H | H | Me |
| Me | 1-CH₃—c-Pr | Me | H | H | H | H | H | Me |
| Me | 2-CH₃—c-Pr | Me | H | H | H | H | H | Me |
| Me | 1,1'-bicyclopropyl-2-yl | Me | H | H | H | H | H | Me |
| Me | 1,1'-bicyclopropyl-1-yl | Me | H | H | H | H | H | Me |
| Me | (1R,2S)-1,1'-bicyclopropyl-2-yl | Me | H | H | H | H | H | Me |

R¹ is NHR³, Y is Cl, the metal cyanide reagent is sodium cyanide, X is NR¹³ and n is 0.

| R² | R³ | R⁵ | R⁶ | R⁷ | R⁸ | R⁹ | R¹⁰ | R¹³ |
|---|---|---|---|---|---|---|---|---|
| Me | H | Me | H | H | H | H | H | Me |
| Me | Me | Me | H | H | H | H | H | Me |
| Me | Et | Me | H | H | H | H | H | Me |
| Me | n-Pr | Me | H | H | H | H | H | Me |
| Me | i-Pr | Me | H | H | H | H | H | Me |
| Me | n-Bu | Me | H | H | H | H | H | Me |
| Me | i-Bu | Me | H | H | H | H | H | Me |
| Me | s-Bu | Me | H | H | H | H | H | Me |
| Me | t-Bu | Me | H | H | H | H | H | Me |
| Me | c-Pr | Me | H | H | H | H | H | Me |
| Me | c-PrCH₂ | Me | H | H | H | H | H | Me |
| Me | 1-CH₃—c-Pr | Me | H | H | H | H | H | Me |
| Me | 2-CH₃—c-Pr | Me | H | H | H | H | H | Me |
| Me | 1,1'-bicyclopropyl-2-yl | Me | H | H | H | H | H | Me |
| Me | 1,1'-bicyclopropyl-1-yl | Me | H | H | H | H | H | Me |
| Me | (1R,2S)-1,1'-bicyclopropyl-2-yl | Me | H | H | H | H | H | Me |

R¹ is NHR³, Y is Br, the metal cyanide reagent is sodium cyanide, X is NR¹³ and n is 0.

| R² | R³ | R⁵ | R⁶ | R⁷ | R⁸ | R⁹ | R¹⁰ | R¹³ |
|---|---|---|---|---|---|---|---|---|
| Cl | H | Me | H | H | H | H | H | Me |
| Cl | Me | Me | H | H | H | H | H | Me |
| Cl | Et | Me | H | H | H | H | H | Me |
| Cl | n-Pr | Me | H | H | H | H | H | Me |
| Cl | i-Pr | Me | H | H | H | H | H | Me |
| Cl | n-Bu | Me | H | H | H | H | H | Me |
| Cl | i-Bu | Me | H | H | H | H | H | Me |
| Cl | s-Bu | Me | H | H | H | H | H | Me |
| Cl | t-Bu | Me | H. | H | H | H | H | Me |
| Cl | c-Pr | Me | H | H | H | H | H | Me |
| Cl | c-PrCH₂ | Me | H | H | H | H | H | Me |
| Cl | 1-CH₃—c-Pr | Me | H | H | H | H | H | Me |
| Cl | 2-CH₃—c-Pr | Me | H | H | H | H | H | Me |
| Cl | 1,1'-bicyclopropyl-2-yl | Me | H | H | H | H | H | Me |
| Cl | 1,1'-bicyclopropyl-1-yl | Me | H | H | H | H | H | Me |
| Cl | (1S,2R)-1,1'-bicyclopropyl-2-yl | Me | H | H | H | H | H | Me |
| Cl | (1R,2R)-1,1'-bicyclopropyl-2-yl | Me | H | H | H | H | H | Me |

| R² | R³ | R⁵ | R⁶ | R⁷ | R⁸ | R⁹ | R¹⁰ | R¹¹ | R¹² | R¹³ |
|---|---|---|---|---|---|---|---|---|---|---|

R¹ is NHR³, Y is Br, the metal cyanide reagent is sodium cyanide, X is NR¹³ and n is 1.

| R² | R³ | R⁵ | R⁶ | R⁷ | R⁸ | R⁹ | R¹⁰ | R¹¹ | R¹² | R¹³ |
|---|---|---|---|---|---|---|---|---|---|---|
| Me | H | H | H | H | Me | Me | H | H | H | H |
| Me | Me | H | H | H | Me | Me | H | H | H | H |
| Me | Et | H | H | H | Me | Me | H | H | H | H |
| Me | n-Pr | H | H | H | Me | Me | H | H | H | H |
| Me | i-Pr | H | H | H | Me | Me | H | H | H | H |
| Me | n-Bu | H | H | H | Me | Me | H | H | H | H |
| Me | i-Bu | H | H | H | Me | Me | H | H | H | H |
| Me | s-Bu | H | H | H | Me | Me | H | H | H | H |
| Me | t-Bu | H | H | H | Me | Me | H | H | H | H |
| Me | c-Pr | H | H | H | Me | Me | H | H | H | H |
| Me | c-PrCH₂ | H | H | H | Me | Me | H | H | H | H |
| Me | 1-CH₃—c-Pr | H | H | H | Me | Me | H | H | H | H |

TABLE 1-continued

| Me | 2-CH₃—c-Pr | H | H | H | Me | Me | H | H | H | H |
|----|------------|---|---|---|----|----|---|---|---|---|
| Me | 1,1'-bicyclopropyl-2-yl | H | H | H | Me | Me | H | H | H | H |
| Me | 1,1'-bicyclopropyl-1-yl | H | H | H | Me | Me | H | H | H | H |
| Me | (1R,2R)-1,1'-bicyclopropyl-2-yl | H | H | H | Me | Me | H | H | H | H |
| Me | H | Me | H | H | H | H | H | H | H | Me |
| Me | Me | Me | H | H | H | H | H | H | H | Me |
| Me | Et | Me | H | H | H | H | H | H | H | Me |
| Me | n-Pr | Me | H | H | H | H | H | H | H | Me |
| Me | i-Pr | Me | H | H | H | H | H | H | H | Me |
| Me | n-Bu | Me | H | H | H | H | H | H | H | Me |
| Me | i-Bu | Me | H | H | H | H | H | H | H | Me |
| Me | s-Bu | Me | H | H | H | H | H | H | H | Me |
| Me | t-Bu | Me | H | H | H | H | H | H | H | Me |
| Me | c-Pr | Me | H | H | H | H | H | H | H | Me |
| Me | c-PrCH₂ | Me | H | H | H | H | H | H | H | Me |
| Me | 1-CH₃—c-Pr | Me | H | H | H | H | H | H | H | Me |
| Me | 2-CH₃—c-Pr | Me | H | H | H | H | H | H | H | Me |
| Me | 1,1'-bicyclopropyl-2-yl | Me | H | H | H | H | H | H | H | Me |
| Me | 1,1'-bicyclopropyl-1-yl | Me | H | H | H | H | H | H | H | Me |
| Me | (1S,2R)-1,1'-bicyclopropyl-2-yl | Me | H | H | H | H | H | H | H | Me |
| Me | (1R,2R)-1,1'-bicyclopropyl-2-yl | Me | H | H | H | H | H | H | H | Me |

R¹ is NHR³, Y is Cl, the metal cyanide reagent is sodium cyanide, X is NR¹³ and n is 1.

| Me | H | H | H | H | Me | Me | H | H | H | H |
|----|---|---|---|---|----|----|---|---|---|---|
| Me | Me | H | H | H | Me | Me | H | H | H | H |
| Me | Et | H | H | H | Me | Me | H | H | H | H |
| Me | n-Pr | H | H | H | Me | Me | H | H | H | H |
| Me | i-Pr | H | H | H | Me | Me | H | H | H | H |
| Me | n-Bu | H | H | H | Me | Me | H | H | H | H |
| Me | i-Bu | H | H | H | Me | Me | H | H | H | H |
| Me | s-Bu | H | H | H | Me | Me | H | H | H | H |
| Me | t-Bu | H | H | H | Me | Me | H | H | H | H |
| Me | c-Pr | H | H | H | Me | Me | H | H | H | H |
| Me | c-PrCH₂ | H | H | H | Me | Me | H | H | H | H |
| Me | 1-CH₃—c-Pr | H | H | H | Me | Me | H | H | H | H |
| Me | 2-CH₃—c-Pr | H | H | H | Me | Me | H | H | H | H |
| Me | 1,1'-bicyclopropyl-2-yl | H | H | H | Me | Me | H | H | H | H |
| Me | 1,1'-bicyclopropyl-1-yl | H | H | H | Me | Me | H | H | H | H |
| Me | (1R,2R)-1,1'-bicyclopropyl-2-yl | H | H | H | Me | Me | H | H | H | H |
| Me | H | Me | H | H | H | H | H | H | H | Me |
| Me | Me | Me | H | H | H | H | H | H | H | Me |
| Me | Et | Me | H | H | H | H | H | H | H | Me |
| Me | n-Pr | Me | H | H | H | H | H | H | H | Me |
| Me | i-Pr | Me | H | H | H | H | H | H | H | Me |
| Me | n-Bu | Me | H | H | H | H | H | H | H | Me |
| Me | i-Bu | Me | H | H | H | H | H | H | H | Me |
| Me | s-Bu | Me | H | H | H | H | H | H | H | Me |
| Me | t-Bu | Me | H | H | H | H | H | H | H | Me |
| Me | c-Pr | Me | H | H | H | H | H | H | H | Me |
| Me | c-PrCH₂ | Me | H | H | H | H | H | H | H | Me |
| Me | 1-CH₃—c-Pr | Me | H | H | H | H | H | H | H | Me |
| Me | 2-CH₃—c-Pr | Me | H | H | H | H | H | H | H | Me |
| Me | 1,1'-bicyclopropyl-2-yl | Me | H | H | H | H | H | H | H | Me |
| Me | 1,1'-bicyclopropyl-1-yl | Me | H | H | H | H | H | H | H | Me |
| Me | (1S,2R)-1,1'-bicyclopropyl-2-yl | Me | H | H | H | H | H | H | H | Me |
| Me | (1R,2R)-1,1'-bicyclopropyl-2-yl | Me | H | H | H | H | H | H | H | Me |

| R² | R⁴ | R⁵ | R⁶ | R⁷ | R¹⁰ | R¹¹ | R¹² | R¹³ |
|----|----|----|----|----|-----|-----|-----|-----|

R¹ is OR⁴, Y is Br, metal cyanide reagent is sodium cyanide, X is NR¹³ and n is 0.

| Me | H | Me | H | H | H | H | H | Me |
|----|---|----|----|---|---|---|---|----|
| Me | Me | Me | H | H | H | H | H | Me |
| Me | Et | Me | H | H | H | H | H | Me |
| Me | n-Pr | Me | H | H | H | H | H | Me |
| Me | i-Pr | Me | H | H | H | H | H | Me |

TABLE 1-continued

| R² | R³ | R⁵ | R⁶ | R⁷ | R¹⁰ | R¹¹ | R¹² | R¹³ |
|---|---|---|---|---|---|---|---|---|
| Me | n-Bu | Me | H | H | H | H | H | Me |
| Me | i-Bu | Me | H | H | H | H | H | Me |
| Me | s-Bu | Me | H | H | H | H | H | Me |
| Me | t-Bu | Me | H | H | H | H | H | Me |

R¹ is OR⁴, Y is Cl, the metal cyanide reagent is sodium cyanide, X is NR¹³ and n is 0.

| R² | R³ | R⁵ | R⁶ | R⁷ | R¹⁰ | R¹¹ | R¹² | R¹³ |
|---|---|---|---|---|---|---|---|---|
| Me | H | Me | H | H | H | H | H | Me |
| Me | Me | Me | H | H | H | H | H | Me |
| Me | Et | Me | H | H | H | H | H | Me |
| Me | n-Pr | Me | H | H | H | H | H | Me |
| Me | i-Pr | Me | H | H | H | H | H | Me |
| Me | n-Bu | Me | H | H | H | H | H | Me |
| Me | i-Bu | Me | H | H | H | H | H | Me |
| Me | t-Bu | Me | H | H | H | H | H | Me |

R¹ is OR⁴, Y is Br, the metal cyanide reagent is sodium cyanide, X is NR¹³ and n is 0.

| R² | R³ | R⁵ | R⁶ | R⁷ | R¹⁰ | R¹¹ | R¹² | R¹³ |
|---|---|---|---|---|---|---|---|---|
| Cl | H | Me | H | H | H | H | H | Me |
| Cl | Me | Me | H | H | H | H | H | Me |
| Cl | Et | Me | H | H | H | H | H | Me |
| Cl | n-Pr | Me | H | H | H | H | H | Me |
| Cl | i-Pr | Me | H | H | H | H | H | Me |
| Cl | n-Bu | Me | H | H | H | H | H | Me |
| Cl | i-Bu | Me | H | H | H | H | H | Me |
| Cl | s-Bu | Me | H | H | H | H | H | Me |
| Cl | t-Bu | Me | H | H | H | H | H | Me |

| R² | R³ | R⁵ | R⁶ | R⁷ | R¹⁰ | R¹¹ | R¹² | R¹³ |
|---|---|---|---|---|---|---|---|---|

R¹ is NHR³, Y is Br, the metal cyanide reagent is potassium hexacyanoferrate(II), X is NR¹³ and n is 0.

| R² | R³ | R⁵ | R⁶ | R⁷ | R¹⁰ | R¹¹ | R¹² | R¹³ |
|---|---|---|---|---|---|---|---|---|
| Me | H | Me | H | H | H | H | H | Me |
| Me | Me | Me | H | H | H | H | H | Me |
| Me | Et | Me | H | H | H | H | H | Me |
| Me | n-Pr | Me | H | H | H | H | H | Me |
| Me | i-Pr | Me | H | H | H | H | H | Me |
| Me | n-Bu | Me | H | H | H | H | H | Me |
| Me | i-Bu | Me | H | H | H | H | H | Me |
| Me | s-Bu | Me | H. | H | H | H | H | Me |
| Me | t-Bu | Me | H | H | H | H | H | Me |
| Me | c-Pr | Me | H | H | H | H | H | Me |
| Me | c-PrCH₂ | Me | H | H | H | H | H | Me |
| Me | 1-CH₃—c-Pr | Me | H | H | H | H | H | Me |
| Me | 2-CH₃—c-Pr | Me | H | H | H | H | H | Me |
| Me | 1,1'-bicyclopropyl-2-yl | Me | H | H | H | H | H | Me |
| Me | 1,1'-bicyclopropyl-1-yl | Me | H | H | H | H | H | Me |
| Me | (1R,2S)-1,1'-bicyclopropyl-2-yl | Me | H | H | H | H | H | Me |

R¹ is NHR³, Y is Cl, the metal cyanide reagent is potassium hexacyanoferrate(II), X is NR¹³ and n is 0.

| R² | R³ | R⁵ | R⁶ | R⁷ | R¹⁰ | R¹¹ | R¹² | R¹³ |
|---|---|---|---|---|---|---|---|---|
| Me | H | Me | H | H | H | H | H | Me |
| Me | Me | Me | H | H | H | H | H | Me |
| Me | Et | Me | H | H | H | H | H | Me |
| Me | n-Pr | Me | H | H | H | H | H | Me |
| Me | i-Pr | Me | H | H | H | H | H | Me |
| Me | n-Bu | Me | H | H | H | H | H | Me |
| Me | i-Bu | Me | H | H | H | H | H | Me |
| Me | s-Bu | Me | H | H | H | H | H | Me |
| Me | t-Bu | Me | H | H | H | H | H | Me |
| Me | c-Pr | Me | H | H | H | H | H | Me |
| Me | c-PrCH₂ | Me | H | H | H | H | H | Me |
| Me | 1-CH₃—c-Pr | Me | H | H | H | H | H | Me |
| Me | 2-CH₃—c-Pr | Me | H | H | H | H | H | Me |
| Me | 1,1'-bicyclopropyl-2-yl | Me | H | H | H | H | H | Me |
| Me | 1,1'-bicyclopropyl-1-yl | Me | H | H | H | H | H | Me |
| Me | (1R,2S)-1,1'-bicyclopropyl-2-yl | Me | H | H | H | H | H | Me |

| R² | R³ | R⁵ | R⁶ | R⁷ | R⁸ | R⁹ | R¹⁰ | R¹¹ | R¹² | R¹³ |
|---|---|---|---|---|---|---|---|---|---|---|

R¹ is NHR³, Y is Br, the metal cyanide reagent is potassium hexacyanoferrate(II), X is NR¹³ and n is 1.

| R² | R³ | R⁵ | R⁶ | R⁷ | R⁸ | R⁹ | R¹⁰ | R¹¹ | R¹² | R¹³ |
|---|---|---|---|---|---|---|---|---|---|---|
| Me | H | H | H | H | Me | Me | H | H | H | H |
| Me | Me | H | H | H | Me | Me | H | H | H | H |
| Me | Et | H | H | H | Me | Me | H | H | H | H |
| Me | n-Pr | H | H | H | Me | Me | H | H | H | H |
| Me | i-Pr | H | H | H | Me | Me | H | H | H | H |

TABLE 1-continued

| Me | n-Bu | H | H | H | Me | Me | H | H | H | H |
|---|---|---|---|---|---|---|---|---|---|---|
| Me | i-Bu | H | H | H | Me | Me | H | H | H | H |
| Me | s-Bu | H | H | H | Me | Me | H | H | H | H |
| Me | t-Bu | H | H | H | Me | Me | H | H | H | H |
| Me | c-Pr | H | H | H | Me | Me | H | H | H | H |
| Me | c-PrCH$_2$ | H | H | H | Me | Me | H | H | H | H |
| Me | 1-CH$_3$—c-Pr | H | H | H | Me | Me | H | H | H | H |
| Me | 2-CH$_3$—c-Pr | H | H | H | Me | Me | H | H | H | H |
| Me | 1,1'-bicyclopropyl-2-yl | H | H | H | Me | Me | H | H | H | H |
| Me | 1,1'-bicyclopropyl-1-yl | H | H | H | Me | Me | H | H | H | H |
| Me | (1R,2R)-1,1'-bicyclopropyl-2-yl | H | H | H | Me | Me | H | H | H | H |
| Me | H | Me | H | H | H | H | H | H | H | Me |
| Me | Me | Me | H | H | H | H | H | H | H | Me |
| Me | Et | Me | H | H | H | H | H | H | H | Me |
| Me | n-Pr | Me | H | H | H | H | H | H | H | Me |
| Me | i-Pr | Me | H | H | H | H | H | H | H | Me |
| Me | n-Bu | Me | H | H | H | H | H | H | H | Me |
| Me | i-Bu | Me | H | H | H | H | H | H | H | Me |
| Me | s-Bu | Me | H | H | H | H | H | H | H | Me |
| Me | t-Bu | Me | H | H | H | H | H | H | H | Me |
| Me | c-Pr | Me | H | H | H | H | H | H | H | Me |
| Me | c-PrCH$_2$ | Me | H | H | H | H | H | H | H | Me |
| Me | 1-CH$_3$—c-Pr | Me | H | H | H | H | H | H | H | Me |
| Me | 2-CH$_3$—c-Pr | Me | H | H | H | H | H | H | H | Me |
| Me | 1,1'-bicyclopropyl-2-yl | Me | H | H | H | H | H | H | H | Me |
| Me | 1,1'-bicyclopropyl-1-yl | Me | H | H | H | H | H | H | H | Me |
| Me | (1S,2R)-1,1'-bicyclopropyl-2-yl | Me | H | H | H | H | H | H | H | Me |
| Me | (1R,2R)-1,1'-bicyclopropyl-2-yl | Me | H | H | H | H | H | H | H | Me |

Table 2 illustrates particular transformations to prepare compounds of Formula 5 from compounds of Formula 2 according to a method of the present invention. Conversion of the compound of Formula 1 to the compound of Formula 5 can, for example, be accomplished according to the method of Scheme 7 using a sulfonyl chloride such as methanesulfonyl chloride in the presence of a solvent such as acetonitrile and a base such as 3-picoline. For these transformations, the metal cyanide reagent is sodium cyanide, the copper(I) salt reagent and the iodide salt reagent are copper(I) iodide, and Formula 3 is N,N'-dimethylethylenediamine (i.e. n is 0, X is NR$^{13}$, R$^6$, R$^7$, R$^{10}$, R$^{11}$ and R$^{12}$ are hydrogen, and R$^5$ and R$^{13}$ are methyl).

TABLE 2

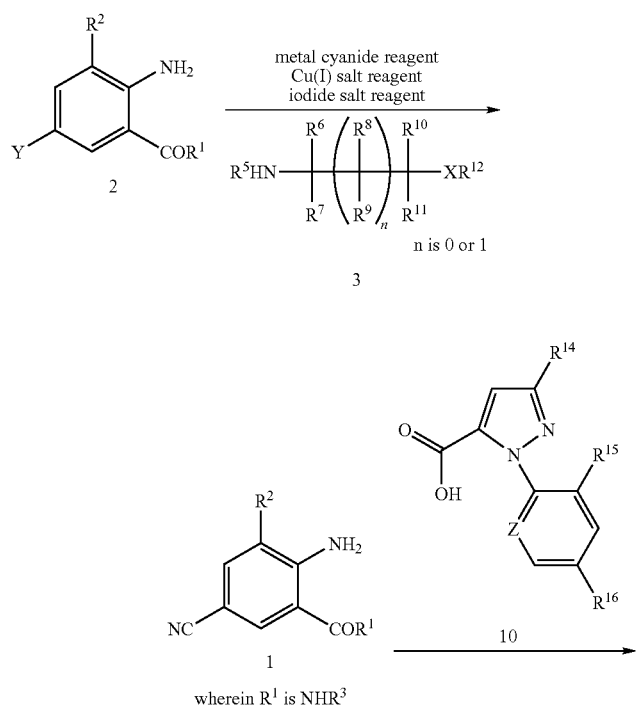

TABLE 2-continued

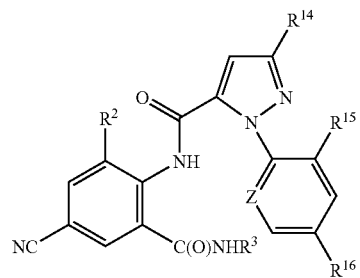

| R³ | R¹⁴ | R¹⁵ | R³ | R¹⁴ | R¹⁵ |
|---|---|---|---|---|---|
| R² is Me, Y is Br, R¹⁶ is H and Z is N. | | | R² is Cl, Y is Br, R¹⁶ is H and Z is N. | | |
| H | Br | F | H | Br | F |
| Me | Br | F | Me | Br | F |
| Et | Br | F | Et | Br | F |
| n-Pr | Br | F | n-Pr | Br | F |
| i-Pr | Br | F | i-Pr | Br | F |
| n-Bu | Br | F | n-Bu | Br | F |
| i-Bu | Br | F | i-Bu | Br | F |
| s-Bu | Br | F | s-Bu | Br | F |
| t-Bu | Br | F | t-Bu | Br | F |
| c-Pr | Br | F | c-Pr | Br | F |
| c-PrCH₂ | Br | F | c-PrCH₂ | Br | F |
| 1-CH₃—c-Pr | Br | F | 1-CH₃—c-Pr | Br | F |
| 2-CH₃—c-Pr | Br | F | 2-CH₃—c-Pr | Br | F |
| 1,1'-bicyclopropyl-2-yl | Br | F | 1,1'-bicyclopropyl-2-yl | Br | F |
| 1,1'-bicyclopropyl-1-yl | Br | F | 1,1'-bicyclopropyl-1-yl | Br | F |
| (1R,2S)-1,1'-bicyclopropyl-2-yl | Br | F | (1R,2S)-1,1'-bicyclopropyl-2-yl | Br | F |
| H | Br | Cl | H | Br | Cl |
| Me | Br | Cl | Me | Br | Cl |
| Et | Br | Cl | Et | Br | Cl |
| n-Pr | Br | Cl | n-Pr | Br | Cl |
| i-Pr | Br | Cl | i-Pr | Br | Cl |
| n-Bu | Br | Cl | n-Bu | Br | Cl |
| i-Bu | Br | Cl | i-Bu | Br | Cl |
| s-Bu | Br | Cl | s-Bu | Br | Cl |
| t-Bu | Br | Cl | t-Bu | Br | Cl |
| c-Pr | Br | Cl | c-Pr | Br | Cl |
| c-PrCH₂ | Br | Cl | c-PrCH₂ | Br | Cl |
| 1-CH₃—c-Pr | Br | Cl | 1-CH₃c-Pr | Br | Cl |
| 2-CH₃—c-Pr | Br | Cl | 2-CH₃c-Pr | Br | Cl |
| 1,1'-bicyclopropyl-2-yl | Br | Cl | 1,1'-bicyclopropyl-2-yl | Br | Cl |
| 1,1'-bicyclopropyl-1-yl | Br | Cl | 1,1'-bicyclopropyl-1-yl | Br | Cl |
| (1R,2R)-1,1'-bicyclopropyl-2-yl | Br | Cl | (1R,2R)-1,1'-bicyclopropyl-2-yl | Br | Cl |
| H | Br | Br | H | Br | Br |
| Me | Br | Br | Me | Br | Br |
| Et | Br | Br | Et | Br | Br |
| n-Pr | Br | Br | n-Pr | Br | Br |
| i-Pr | Br | Br | i-Pr | Br | Br |
| n-Bu | Br | Br | n-Bu | Br | Br |
| i-Bu | Br | Br | i-Bu | Br | Br |
| s-Bu | Br | Br | s-Bu | Br | Br |
| t-Bu | Br | Br | t-Bu | Br | Br |
| c-Pr | Br | Br | c-Pr | Br | Br |
| c-PrCH₂ | Br | Br | c-PrCH₂ | Br | Br |
| 1-CH₃—c-Pr | Br | Br | 1-CH₃—c-Pr | Br | Br |
| 2-CH₃—c-Pr | Br | Br | 2-CH₃—c-Pr | Br | Br |
| 1,1'-bicyclopropyl-2-yl | Br | Br | 1,1'-bicyclopropyl-2-yl | Br | Br |
| 1,1'-bicyclopropyl-1-yl | Br | Br | 1,1'-bicyclopropyl-1-yl | Br | Br |
| H | Cl | F | H | Cl | F |
| Me | Cl | F | Me | Cl | F |
| Et | Cl | F | Et | Cl | F |
| n-Pr | Cl | F | n-Pr | Cl | F |
| i-Pr | Cl | F | i-Pr | Cl | F |
| n-Bu | Cl | F | n-Bu | Cl | F |
| i-Bu | Cl | F | i-Bu | Cl | F |
| s-Bu | Cl | F | s-Bu | Cl | F |
| t-Bu | Cl | F | t-Bu | Cl | F |
| c-Pr | Cl | F | c-Pr | Cl | F |
| c-PrCH₂ | Cl | F | c-PrCH₂ | Cl | F |
| 1-CH₃—c-Pr | Cl | F | 1-CH₃—c-Pr | Cl | F |
| 2-CH₃—c-Pr | Cl | F | 2-CH₃—c-Pr | Cl | F |

TABLE 2-continued

| | | | | | |
|---|---|---|---|---|---|
| 1,1'-bicyclopropyl-2-yl | Cl | F | 1,1'-bicyclopropyl-2-yl | Cl | F |
| 1,1'-bicyclopropyl-1-yl | Cl | F | 1,1'-bicyclopropyl-1-yl | Cl | F |
| (1S,2R)-1,1'-bicyclopropyl-2-yl | Cl | F | (1S,2R)-1,1'-bicyclopropyl-2-yl | Cl | F |
| H | Cl | Cl | H | Cl | Cl |
| Me | Cl | Cl | Me | Cl | Cl |
| Et | Cl | Cl | Et | Cl | Cl |
| n-Pr | Cl | Cl | n-Pr | Cl | Cl |
| i-Pr | Cl | Cl | i-Pr | Cl | Cl |
| n-Bu | Cl | Cl | n-Bu | Cl | Cl |
| i-Bu | Cl | Cl | i-Bu | Cl | Cl |
| s-Bu | Cl | Cl | s-Bu | Cl | Cl |
| t-Bu | Cl | Cl | t-Bu | Cl | Cl |
| c-Pr | Cl | Cl | c-Pr | Cl | Cl |
| c-PrCH$_2$ | Cl | Cl | c-PrCH$_2$ | Cl | Cl |
| 1-CH$_3$—c-Pr | Cl | Cl | 1-CH$_3$—c-Pr | Cl | Cl |
| 2-CH$_3$—c-Pr | Cl | Cl | 2-CH$_3$—c-Pr | Cl | Cl |
| 1,1'-bicyclopropyl-2-yl | Cl | Cl | 1,1'-bicyclopropyl-2-yl | Cl | Cl |
| 1,1'-bicyclopropyl-1-yl | Cl | Cl | 1,1'-bicyclopropyl-1-yl | Cl | Cl |
| (1R,2R)-1,1'-bicyclopropyl-2-yl | Cl | Cl | (1R,2R)-1,1'-bicyclopropyl-2-yl | Cl | Cl |
| H | Cl | Br | H | Cl | Br |
| Me | Cl | Br | Me | Cl | Br |
| Et | Cl | Br | Et | Cl | Br |
| n-Pr | Cl | Br | n-Pr | Cl | Br |
| i-Pr | Cl | Br | i-Pr | Cl | Br |
| n-Bu | Cl | Br | n-Bu | Cl | Br |
| i-Bu | Cl | Br | i-Bu | Cl | Br |
| s-Bu | Cl | Br | s-Bu | Cl | Br |
| t-Bu | Cl | Br | t-Bu | Cl | Br |
| c-Pr | Cl | Br | c-Pr | Cl | Br |
| c-PrCH$_2$ | Cl | Br | c-PrCH$_2$ | Cl | Br |
| 1-CH$_3$—c-Pr | Cl | Br | 1-CH$_3$—c-Pr | Cl | Br |
| 2-CH$_3$—c-Pr | Cl | Br | 2-CH$_3$—c-Pr | Cl | Br |
| 1,1'-bicyclopropyl-2-yl | Cl | Br | 1,1'-bicyclopropyl-2-yl | Cl | Br |
| 1,1'-bicyclopropyl-1-yl | Cl | Br | 1,1'-bicyclopropyl-1-yl | Cl | Br |
| H | CF$_3$ | F | H | CF$_3$ | F |
| Me | CF$_3$ | F | Me | CF$_3$ | F |
| t-Bu | CF$_3$ | F | t-Bu | CF$_3$ | F |
| 1-CH$_3$—c-Pr | CF$_3$ | F | 1-CH$_3$—c-Pr | CF$_3$ | F |
| 2-CH$_3$—c-Pr | CF$_3$ | F | 2-CH$_3$—c-Pr | CF$_3$ | F |
| 1-1'-bicyclopropyl-1-yl | CF$_3$ | F | 1,1'-bicyclopropyl-1-yl | CF$_3$ | F |
| (1R,2S)-1,1'-bicyclopropyl-2-yl | CF$_3$ | F | (1R,2S)-1,1'-bicyclopropyl-2-yl | CF$_3$ | F |
| H | CF$_3$ | Cl | H | CF$_3$ | Cl |
| Me | CF$_3$ | Cl | Me | CF$_3$ | Cl |
| t-Bu | CF$_3$ | Cl | t-Bu | CF$_3$ | Cl |
| 1-CH$_3$—c-Pr | CF$_3$ | Cl | 1-CH$_3$—c-Pr | CF$_3$ | Cl |
| 2-CH$_3$—c-Pr | CF$_3$ | Cl | 2-CH$_3$—c-Pr | CF$_3$ | Cl |
| 1,1'-bicyclopropyl-2-yl | CF$_3$ | Cl | 1,1'-bicyclopropyl-2-yl | CF$_3$ | Cl |
| 1,1'-bicyclopropyl-1-yl | CF$_3$ | Cl | 1,1'-bicyclopropyl-1-yl | CF$_3$ | Cl |
| H | CF$_3$ | Br | H | CF$_3$ | Br |
| Me | CF$_3$ | Br | Me | CF$_3$ | Br |
| t-Bu | CF$_3$ | Br | t-Bu | CF$_3$ | Br |
| 1-CH$_3$—c-Pr | CF$_3$ | Br | 1-CH$_3$—c-Pr | CF$_3$ | Br |
| 2-CH$_3$—c-Pr | CF$_3$ | Br | 2-CH$_3$—c-Pr | CF$_3$ | Br |
| 1,1'-bicyclopropyl-2-yl | CF$_3$ | Br | 1,1'-bicyclopropyl-2-yl | CF$_3$ | Br |
| H | OCH$_2$CF$_3$ | F | H | OCH$_2$CF$_3$ | F |
| Me | OCH$_2$CF$_3$ | F | Me | OCH$_2$CF$_3$ | F |
| t-Bu | OCH$_2$CF$_3$ | F | t-Bu | OCH$_2$CF$_3$ | F |
| 1,1'-bicyclopropyl-1-yl | OCH$_2$CF$_3$ | F | 1,1'-bicyclopropyl-1-yl | OCH$_2$CF$_3$ | F |
| H | OCH$_2$CF$_3$ | Cl | H | OCH$_2$CF$_3$ | Cl |
| Me | OCH$_2$CF$_3$ | Cl | Me | OCH$_2$CF$_3$ | Cl |
| t-Bu | OCH$_2$CF$_3$ | Cl | t-Bu | OCH$_2$CF$_3$ | Cl |
| 1,1'-bicyclopropyl-1-yl | OCH$_2$CF$_3$ | Cl | 1,1'-bicyclopropyl-1-yl | OCH$_2$CF$_3$ | Cl |
| H | OCH$_2$CF$_3$ | Br | H | OCH$_2$CF$_3$ | Br |
| Me | OCH$_2$CF$_3$ | Br | Me | OCH$_2$CF$_3$ | Br |
| t-Bu | OCH$_2$CF$_3$ | Br | t-Bu | OCH$_2$CF$_3$ | Br |
| 1,1'-bicyclopropyl-1-yl | OCH$_2$CF$_3$ | Br | 1,1'-bicyclopropyl-1-yl | OCH$_2$CF$_3$ | Br |
| H | OCF$_2$H | F | H | OCF$_2$H | F |
| Me | OCF$_2$H | F | Me | OCF$_2$H | F |
| t-Bu | OCF$_2$H | F | t-Bu | OCF$_2$H | F |
| 1,1'-bicyclopropyl-1-yl | OCF$_2$H | F | 1,1'-bicyclopropyl-1-yl | OCF$_2$H | F |
| H | OCF$_2$H | Cl | H | OCF$_2$H | Cl |
| Me | OCF$_2$H | Cl | Me | OCF$_2$H | Cl |
| t-Bu | OCF$_2$H | Cl | t-Bu | OCF$_2$H | Cl |
| 1,1'-bicyclopropyl-1-yl | OCF$_2$H | Cl | 1,1'-bicyclopropyl-1-yl | OCF$_2$H | Cl |
| H | OCF$_2$H | Br | H | OCF$_2$H | Br |
| Me | OCF$_2$H | Br | Me | OCF$_2$H | Br |
| t-Bu | OCF$_2$H | Br | t-Bu | OCF$_2$H | Br |

TABLE 2-continued

| R² is Me, Y is Br, R¹⁶ is H and Z is CH. | | | R² is Cl, Y is Br, R¹⁶ is H and Z is CH. | | |
|---|---|---|---|---|---|
| H | Br | F | H | Br | F |
| Me | Br | F | Me | Br | F |
| t-Bu | Br | F | t-Bu | Br | F |
| c-Pr | Br | F | c-Pr | Br | F |
| c-PrCH₂ | Br | F | c-PrCH₂ | Br | F |
| 1,1'-bicyclopropyl-2-yl | Br | F | 1,1'-bicyclopropyl-2-yl | Br | F |
| 1,1'-bicyclopropyl-1-yl | Br | F | 1,1'-bicyclopropyl-1-yl | Br | F |
| (1R,2S)-1,1'-bicyclopropyl-2-yl | Br | F | (1R,2S)-1,1'-bicyclopropyl-2-yl | Br | F |
| (1R,2R)-1,1'-bicyclopropyl-2-yl | Br | F | (1R,2R)-1,1'-bicyclopropyl-2-yl | Br | F |
| H | Br | Cl | H | Br | Cl |
| Me | Br | Cl | Me | Br | Cl |
| t-Bu | Br | Cl | t-Bu | Br | Cl |
| c-Pr | Br | Cl | c-Pr | Br | Cl |
| c-PrCH₂ | Br | Cl | c-PrCH₂ | Br | Cl |
| 1,1'-bicyclopropyl-2-yl | Br | Cl | 1,1'-bicyclopropyl-2-yl | Br | Cl |
| 1,1'-bicyclopropyl-1-yl | Br | Cl | 1,1'-bicyclopropyl-1-yl | Br | Cl |
| H | Br | Br | H | Br | Br |
| Me | Br | Br | Me | Br | Br |
| t-Bu | Br | Br | t-Bu | Br | Br |
| c-Pr | Br | Br | c-Pr | Br | Br |
| c-PrCH₂ | Br | Br | c-PrCH₂ | Br | Br |
| 1,1'-bicyclopropyl-2-yl | Br | Br | 1,1'-bicyclopropyl-2-yl | Br | Br |
| 1,1'-bicyclopropyl-1-yl | Br | Br | 1,1'-bicyclopropyl-1-yl | Br | Br |
| H | Cl | F | H | Cl | F |
| Me | Cl | F | Me | Cl | F |
| t-Bu | Cl | F | t-Bu | Cl | F |
| c-Pr | Cl | F | c-Pr | Cl | F |
| c-PrCH₂ | Cl | F | c-PrCH₂ | Cl | F |
| 1,1'-bicyclopropyl-2-yl | Cl | F | 1,1'-bicyclopropyl-2-yl | Cl | F |
| 1,1'-bicyclopropyl-1-yl | Cl | F | 1,1'-bicyclopropyl-1-yl | Cl | F |
| (1R,2R)-1,1'-bicyclopropyl-2-yl | Cl | F | (1R,2R)-1,1'-bicyclopropyl-2-yl | Cl | F |
| H | Cl | Cl | H | Cl | Cl |
| Me | Cl | Cl | Me | Cl | Cl |
| t-Bu | Cl | Cl | t-Bu | Cl | Cl |
| c-Pr | Cl | Cl | c-Pr | Cl | Cl |
| c-PrCH₂ | Cl | Cl | c-PrCH₂ | Cl | Cl |
| 1,1'-bicyclopropyl-2-yl | Cl | Cl | 1,1'-bicyclopropyl-2-yl | Cl | Cl |
| 1,1'-bicyclopropyl-1-yl | Cl | Cl | 1,1'-bicyclopropyl-1-yl | Cl | Cl |
| (1S,2R)-1,1'-bicyclopropyl-2-yl | Cl | Cl | (1S,2R)-1,1'-bicyclopropyl-2-yl | Cl | Cl |
| H | Cl | Br | H | Cl | Br |
| Me | Cl | Br | Me | Cl | Br |
| t-Bu | Cl | Br | t-Bu | Cl | Br |
| c-Pr | Cl | Br | c-Pr | Cl | Br |
| c-PrCH₂ | Cl | Br | c-PrCH₂ | Cl | Br |
| 1,1'-bicyclopropyl-2-yl | Cl | Br | 1,1'-bicyclopropyl-2-yl | Cl | Br |
| 1,1'-bicyclopropyl-1-yl | Cl | Br | 1,1'-bicyclopropyl-1-yl | Cl | Br |
| H | CF₃ | F | H | CF₃ | F |
| Me | CF₃ | F | Me | CF₃ | F |
| t-Bu | CF₃ | F | t-Bu | CF₃ | F |
| 2-CH₃—c-Pr | CF₃ | F | c-Pr | CF₃ | F |
| 1,1'-bicyclopropyl-2-yl | CF₃ | F | 1,1'-bicyclopropyl-2-yl | CF₃ | F |
| H | CF₃ | Cl | H | CF₃ | Cl |
| Me | CF₃ | Cl | Me | CF₃ | Cl |
| t-Bu | CF₃ | Cl | t-Bu | CF₃ | Cl |
| Me | CF₃ | Cl | Me | CF₃ | Br |
| Et | CF₃ | Br | Et | CF₃ | Br |
| c-Pr | CF₃ | Br | c-Pr | CF₃ | Br |
| c-PrCH₂ | CF₃ | Br | c-PrCH₂ | CF₃ | Br |
| 1,1'-bicyclopropyl-2-yl | CF₃ | Br | 1,1'-bicyclopropyl-2-yl | CF₃ | Br |
| Me | OCH₂CF₃ | F | Me | OCH₂CF₃ | F |
| Et | OCH₂CF₃ | F | Et | OCH₂CF₃ | F |
| c-Pr | OCH₂CF₃ | F | c-Pr | OCH₂CF₃ | Cl |
| c-PrCH₂ | OCH₂CF₃ | Cl | c-PrCH₂ | OCH₂CF₃ | Cl |
| 1,1'-bicyclopropyl-2-yl | OCH₂CF₃ | Cl | 1,1'-bicyclopropyl-2-yl | OCH₂CF₃ | Cl |
| Me | OCH₂CF₃ | Br | Me | OCH₂CF₃ | Br |
| Et | OCH₂CF₃ | Br | Et | OCH₂CF₃ | Br |
| Me | OCF₂H | F | Me | OCF₂H | F |
| Et | OCF₂H | F | Et | OCF₂H | F |
| c-Pr | OCF₂H | Cl | c-Pr | OCF₂H | Cl |
| c-PrCH₂ | OCF₂H | Cl | c-PrCH₂ | OCF₂H | Cl |
| 1,1'-bicyclopropyl-2-yl | OCF₂H | Cl | 1,1'-bicyclopropyl-2-yl | OCF₂H | Cl |
| Me | OCF₂H | Br | Me | OCF₂H | Br |
| Et | OCF₂H | Br | Et | OCF₂H | Br |

TABLE 2-continued

| R² is Me, Y is Br, R¹⁶ is F and Z is N. | | | R² is Cl, Y is Br, R¹⁶ is F and Z is N. | | |
|---|---|---|---|---|---|
| H | Br | F | H | Br | F |
| Me | Br | F | Me | Br | F |
| t-Bu | Br | F | t-Bu | Br | F |
| c-Pr | Br | F | c-Pr | Br | F |
| c-PrCH$_2$ | Br | F | c-PrCH$_2$ | Br | F |
| 1,1'-bicyclopropyl-2-yl | Br | F | 1,1'-bicyclopropyl-2-yl | Br | F |
| 1,1'-bicyclopropyl-1-yl | Br | F | 1,1'-bicyclopropyl-1-yl | Br | F |
| H | Br | Cl | H | Br | Cl |
| Me | Br | Cl | Me | Br | Cl |
| t-Bu | Br | Cl | t-Bu | Br | Cl |
| c-Pr | Br | Cl | c-Pr | Br | Cl |
| c-PrCH$_2$ | Br | Cl | c-PrCH$_2$ | Br | Cl |
| 1,1'-bicyclopropyl-1-yl | Br | Cl | 1,1'-bicyclopropyl-1-yl | Br | Cl |
| H | Br | Br | H | Br | Br |
| Me | Br | Br | Me | Br | Br |
| t-Bu | Br | Br | t-Bu | Br | Br |
| c-Pr | Br | Br | c-Pr | Br | Br |
| c-PrCH$_2$ | Br | Br | c-PrCH$_2$ | Br | Br |
| 1,1'-bicyclopropyl-1-yl | Br | Br | 1,1'-bicyclopropyl-1-yl | Br | Br |
| (1R,2S)-1,1'-bicyclopropyl-2-yl | Br | Br | (1R,2S)-1,1'-bicyclopropyl-2-yl | Br | Br |
| H | Cl | F | H | Cl | F |
| Me | Cl | F | Me | Cl | F |
| t-Bu | Cl | F | t-Bu | Cl | F |
| c-Pr | Cl | F | c-Pr | Cl | F |
| c-PrCH$_2$ | Cl | F | c-PrCH$_2$ | Cl | F |
| 1,1'-bicyclopropyl-2-yl | Cl | F | 1,1'-bicyclopropyl-2-yl | Cl | F |
| H | Cl | Cl | H | Cl | Cl |
| Me | Cl | Cl | Me | Cl | Cl |
| t-Bu | Cl | Cl | t-Bu | Cl | Cl |
| c-Pr | Cl | Cl | c-Pr | Cl | Cl |
| c-PrCH$_2$ | Cl | Cl | c-PrCH$_2$ | Cl | Cl |
| 1,1'-bicyclopropyl-1-yl | Cl | Cl | 1,1'-bicyclopropyl-1-yl | Cl | Cl |
| H | Cl | Br | H | Cl | Br |
| Me | Cl | Br | Me | Cl | Br |
| t-Bu | Cl | Br | t-Bu | Cl | Br |
| c-Pr | Cl | Br | c-Pr | Cl | Br |
| c-PrCH$_2$ | Cl | Br | c-PrCH$_2$ | Cl | Br |
| 1,1'-bicyclopropyl-2-yl | Cl | Br | 1,1'-bicyclopropyl-2-yl | Cl | Br |
| 1,1'-bicyclopropyl-1-yl | Cl | Br | 1,1'-bicyclopropyl-1-yl | Cl | Br |
| H | CF$_3$ | F | H | CF$_3$ | F |
| Me | CF$_3$ | F | Me | CF$_3$ | F |
| t-Bu | CF$_3$ | F | t-Bu | CF$_3$ | F |
| 2-CH$_3$—c-Pr | CF$_3$ | F | c-Pr | CF$_3$ | F |
| 1,1'-bicyclopropyl-2-yl | CF$_3$ | F | 1,1'-bicyclopropyl-2-yl | CF$_3$ | F |
| H | CF$_3$ | Cl | H | CF$_3$ | Cl |
| Me | CF$_3$ | Cl | Me | CF$_3$ | Cl |
| t-Bu | CF$_3$ | Cl | t-Bu | CF$_3$ | Cl |
| Me | CF$_3$ | Br | Me | CF$_3$ | Br |
| Et | CF$_3$ | Br | Et | CF$_3$ | Br |
| c-Pr | CF$_3$ | Br | c-Pr | CF$_3$ | Br |
| c-PrCH$_2$ | CF$_3$ | Br | c-PrCH$_2$ | CF$_3$ | Br |
| 1,1'-bicyclopropyl-2-yl | CF$_3$ | Br | 1,1'-bicyclopropyl-2-yl | CF$_3$ | Br |
| Me | OCH$_2$CF$_3$ | F | Me | OCH$_2$CF$_3$ | F |
| Et | OCH$_2$CF$_3$ | F | Et | OCH$_2$CF$_3$ | F |
| c-Pr | OCH$_2$CF$_3$ | Cl | c-Pr | OCH$_2$CF$_3$ | Cl |
| c-PrCH$_2$ | OCH$_2$CF$_3$ | Cl | c-PrCH$_2$ | OCH$_2$CF$_3$ | Cl |
| 1,1'-bicyclopropyl-1-yl | OCH$_2$CF$_3$ | Cl | 1,1'-bicyclopropyl-1-yl | OCH$_2$CF$_3$ | Cl |
| Me | OCH$_2$CF$_3$ | Br | Me | OCH$_2$CF$_3$ | Br |
| Et | OCH$_2$CF$_3$ | Br | Et | OCH$_2$CF$_3$ | Br |
| Me | OCF$_2$H | F | Me | OCF$_2$H | F |
| Et | OCF$_2$H | F | Et | OCF$_2$H | F |
| c-Pr | OCF$_2$H | Cl | c-Pr | OCF$_2$H | Cl |
| c-PrCH$_2$ | OCF$_2$H | Cl | c-PrCH$_2$ | OCF$_2$H | Cl |
| 1,1'-bicyclopropyl-1-yl | OCF$_2$H | Cl | 1,1'-bicyclopropyl-1-yl | OCF$_2$H | Cl |
| Me | OCF$_2$H | Br | Me | OCF$_2$H | Br |
| Et | OCF$_2$H | Br | Et | OCF$_2$H | Br |

| R² is Me, Y is Br, R¹⁶ is Cl and Z is N. | | | R² is Cl, Y is Br, R¹⁶ is Cl and Z is N. | | |
|---|---|---|---|---|---|
| H | Br | F | H | Br | F |
| Me | Br | F | Me | Br | F |
| t-Bu | Br | F | t-Bu | Br | F |
| c-Pr | Br | F | c-Pr | Br | F |
| c-PrCH$_2$ | Br | F | c-PrCH$_2$ | Br | F |
| 1,1'-bicyclopropyl-2-yl | Br | F | 1,1'-bicyclopropyl-2-yl | Br | F |
| 1,1'-bicyclopropyl-1-yl | Br | F | 1,1'-bicyclopropyl-1-yl | Br | F |
| H | Br | Cl | H | Br | Cl |
| Me | Br | Cl | Me | Br | Cl |

TABLE 2-continued

| | | | | | |
|---|---|---|---|---|---|
| t-Bu | Br | Cl | t-Bu | Br | Cl |
| c-Pr | Br | Cl | c-Pr | Br | Cl |
| c-PrCH$_2$ | Br | Cl | c-PrCH$_2$ | Br | Cl |
| 1,1'-bicyclopropyl-2-yl | Br | Cl | 1,1'-bicyclopropyl-2-yl | Br | Cl |
| (1R,2S)-1,1'-bicyclopropyl-2-yl | Br | Cl | (1R,2S)-1,1'-bicyclopropyl-2-yl | Br | Cl |
| H | Br | Br | H | Br | Br |
| Me | Br | Br | Me | Br | Br |
| t-Bu | Br | Br | t-Bu | Br | Br |
| c-Pr | Br | Br | c-Pr | Br | Br |
| c-PrCH$_2$ | Br | Br | c-PrCH$_2$ | Br | Br |
| 1,1'-bicyclopropyl-1-yl | Br | Br | 1,1'-bicyclopropyl-1-yl | Br | Br |
| (1R,2R)-1,1'-bicyclopropyl-2-yl | Br | Br | (1R,2R)-1,1'-bicyclopropyl-2-yl | Br | Br |
| H | Cl | F | H | Cl | F |
| Me | Cl | F | Me | Cl | F |
| t-Bu | Cl | F | t-Bu | Cl | F |
| c-Pr | Cl | F | c-Pr | Cl | F |
| c-PrCH$_2$ | Cl | F | c-PrCH$_2$ | Cl | F |
| 1,1'-bicyclopropyl-2-yl | Cl | F | 1,1'-bicyclopropyl-2-yl | Cl | F |
| H | Cl | Cl | H | Cl | Cl |
| Me | Cl | Cl | Me | Cl | Cl |
| t-Bu | Cl | Cl | t-Bu | Cl | Cl |
| c-Pr | Cl | Cl | c-Pr | Cl | Cl |
| c-PrCH$_2$ | Cl | Cl | c-PrCH$_2$ | Cl | Cl |
| 1,1'-bicyclopropyl-2-yl | Cl | Cl | 1,1'-bicyclopropyl-2-yl | Cl | Cl |
| 1,1'-bicyclopropyl-1-yl | Cl | Cl | 1,1'-bicyclopropyl-1-yl | Cl | Cl |
| H | Cl | Br | H | Cl | Br |
| Me | Cl | Br | Me | Cl | Br |
| t-Bu | Cl | Br | t-Bu | Cl | Br |
| c-Pr | Cl | Br | c-Pr | Cl | Br |
| c-PrCH$_2$ | Cl | Br | c-PrCH$_2$ | Cl | Br |
| 1,1'-bicyclopropyl-2-yl | Cl | Br | 1,1'-bicyclopropyl-2-yl | Cl | Br |
| 1,1'-bicyclopropyl-1-yl | Cl | Br | 1,1'-bicyclopropyl-1-yl | Cl | Br |
| H | CF$_3$ | F | H | CF$_3$ | F |
| Me | CF$_3$ | F | Me | CF$_3$ | F |
| t-Bu | CF$_3$ | F | t-Bu | CF$_3$ | F |
| 2-CH$_3$—c-Pr | CF$_3$ | F | c-Pr | CF$_3$ | F |
| 1,1'-bicyclopropyl-2-yl | CF$_3$ | F | 1,1'-bicyclopropyl-2-yl | CF$_3$ | F |
| 1,1'-bicyclopropyl-1-yl | CF$_3$ | F | 1,1'-bicyclopropyl-1-yl | CF$_3$ | F |
| H | CF$_3$ | Cl | H | CF$_3$ | Cl |
| Me | CF$_3$ | Cl | Me | CF$_3$ | Cl |
| t-Bu | CF$_3$ | Cl | t-Bu | CF$_3$ | Cl |
| Me | CF$_3$ | Br | Me | CF$_3$ | Br |
| Et | CF$_3$ | Br | Et | CF$_3$ | Br |
| c-Pr | CF$_3$ | Br | c-Pr | CF$_3$ | Br |
| c-PrCH$_2$ | CF$_3$ | Br | c-PrCH$_2$ | CF$_3$ | Br |
| 1,1'-bicyclopropyl-2-yl | CF$_3$ | Br | 1,1'-bicyclopropyl-2-yl | CF$_3$ | Br |
| Me | OCH$_2$CF$_3$ | F | Et | OCH$_2$CF$_3$ | F |
| Et | OCH$_2$CF$_3$ | F | Et | OCH$_2$CF$_3$ | F |
| c-Pr | OCH$_2$CF$_3$ | Cl | c-Pr | OCH$_2$CF$_3$ | Cl |
| c-PrCH$_2$ | OCH$_2$CF$_3$ | Cl | c-PrCH$_2$ | OCH$_2$CF$_3$ | Cl |
| 1,1'-bicyclopropyl-1-yl | OCH$_2$CF$_3$ | Cl | 1,1'-bicyclopropyl-1-yl | OCH$_2$CF$_3$ | Cl |
| Me | OCH$_2$CF$_3$ | Br | Me | OCH$_2$CF$_3$ | Br |
| Et | OCH$_2$CF$_3$ | Br | Et | OCH$_2$CF$_3$ | Br |
| Me | OCF$_2$H | F | Me | OCF$_2$H | F |
| Et | OCF$_2$H | F | Et | OCF$_2$H | F |
| c-Pr | OCF$_2$H | Cl | c-Pr | OCF$_2$H | Cl |
| c-PrCH$_2$ | OCF$_2$H | Cl | c-PrCH$_2$ | OCF$_2$H | Cl |
| 1,1'-bicyclopropyl-2-yl | OCF$_2$H | F | 1,1'-bicyclopropyl-2-yl | OCF$_2$H | F |
| Me | OCF$_2$H | Br | Me | OCF$_2$H | Br |
| Et | OCF$_2$H | Br | Et | OCF$_2$H | Br |

| R$^2$ is Me, Y is Cl, R$^{16}$ is H and Z is N. | | | R$^2$ is Me, Y is Cl, R$^{16}$ is H and Z is N. | | |
|---|---|---|---|---|---|
| H | Br | F | H | Br | Cl |
| Me | Br | F | Me | Br | Cl |
| Et | Br | F | Et | Br | Cl |
| n-Pr | Br | F | n-Pr | Br | Cl |
| i-Pr | Br | F | i-Pr | Br | Cl |
| n-Bu | Br | F | n-Bu | Br | Cl |
| i-Bu | Br | F | i-Bu | Br | Cl |
| s-Bu | Br | F | s-Bu | Br | Cl |
| t-Bu | Br | F | t-Bu | Br | Cl |
| c-Pr | Br | F | c-Pr | Br | Cl |
| c-PrCH$_2$ | Br | F | c-PrCH$_2$ | Br | Cl |
| 1-CH$_3$—c-Pr | Br | F | 1-CH$_3$—c-Pr | Br | Cl |
| 2-CH$_3$—c-Pr | Br | F | 2-CH$_3$—c-Pr | Br | Cl |
| 1,1'-bicyclopropyl-2-yl | Br | F | 1,1'-bicyclopropyl-2-yl | Br | Cl |
| 1,1'-bicyclopropyl-1-yl | Br | F | 1,1'-bicyclopropyl-1-yl | Br | Cl |
| (1R,2S)-1,1'-bicyclopropyl-2-yl | Br | F | (1R,2R)-1,1'-bicyclopropyl-2-yl | Br | Cl |
| H | Br | Br | H | Cl | F |

TABLE 2-continued

| | | | | | |
|---|---|---|---|---|---|
| Me | Br | Br | Me | Cl | F |
| Et | Br | Br | Et | Cl | F |
| n-Pr | Br | Br | n-Pr | Cl | F |
| i-Pr | Br | Br | i-Pr | Cl | F |
| n-Bu | Br | Br | n-Bu | Cl | F |
| i-Bu | Br | Br | i-Bu | Cl | F |
| s-Bu | Br | Br | s-Bu | Cl | F |
| t-Bu | Br | Br | t-Bu | Cl | F |
| c-Pr | Br | Br | c-Pr | Cl | F |
| c-PrCH$_2$ | Br | Br | c-PrCH$_2$ | Cl | F |
| 1-CH$_3$—c-Pr | Br | Br | 1-CH$_3$—c-Pr | Cl | F |
| 2-CH$_3$—c-Pr | Br | Br | 2-CH$_3$—c-Pr | Cl | F |
| 1,1'-bicyclopropyl-2-yl | Br | Br | 1,1'-bicyclopropyl-2-yl | Cl | F |
| 1,1'-bicyclopropyl-1-yl | Br | Br | 1,1'-bicyclopropyl-1-yl | Cl | F |
| (1S,2R)-1,1'-bicyclopropyl-2-yl | Br | Br | (1S,2R)-1,1'-bicyclopropyl-2-yl | Cl | F |
| H | Cl | Cl | H | Cl | Br |
| Me | Cl | Cl | Me | Cl | Br |
| Et | Cl | Cl | Et | Cl | Br |
| n-Pr | Cl | Cl | n-Pr | Cl | Br |
| i-Pr | Cl | Cl | i-Pr | Cl | Br |
| n-Bu | Cl | Cl | n-Bu | Cl | Br |
| i-Bu | Cl | Cl | i-Bu | Cl | Br |
| s-Bu | Cl | Cl | s-Bu | Cl | Br |
| t-Bu | Cl | Cl | t-Bu | Cl | Br |
| c-Pr | Cl | Cl | c-Pr | Cl | Br |
| c-PrCH$_2$ | Cl | Cl | c-PrCH$_2$ | Cl | Br |
| 1-CH$_3$—c-Pr | Cl | Cl | 1-CH$_3$—c-Pr | Cl | Br |
| 2-CH$_3$—c-Pr | Cl | Cl | 2-CH$_3$—c-Pr | Cl | Br |
| 1,1'-bicyclopropyl-2-yl | Cl | Cl | 1,1'-bicyclopropyl-2-yl | Cl | Br |
| 1,1'-bicyclopropyl-1-yl | Cl | Cl | 1,1'-bicyclopropyl-1-yl | Cl | Br |
| (1R,2R)-1,1'-bicyclopropyl-2-yl | Cl | Cl | (1R,2R)-1,1'-bicyclopropyl-2-yl | Cl | Br |
| H | CF$_3$ | F | H | CF$_3$ | Cl |
| Me | CF$_3$ | F | Me | CF$_3$ | Cl |
| t-Bu | CF$_3$ | F | t-Bu | CF$_3$ | Cl |
| 1-CH$_3$—c-Pr | CF$_3$ | F | 1-CH$_3$—c-Pr | CF$_3$ | Cl |
| 2-CH$_3$—c-Pr | CF$_3$ | F | 2-CH$_3$—c-Pr | CF$_3$ | Cl |
| 1,1'-bicyclopropyl-1-yl | CF$_3$ | F | 1,1'-bicyclopropyl-2-yl | CF$_3$ | Cl |
| (1R,2S)-1,1'-bicyclopropyl-2-yl | CF$_3$ | F | 1,1'-bicyclopropyl-1-yl | CF$_3$ | Cl |
| H | CF$_3$ | Br | H | OCH$_2$CF$_3$ | F |
| Me | CF$_3$ | Br | Me | OCH$_2$CF$_3$ | F |
| t-Bu | CF$_3$ | Br | t-Bu | OCH$_2$CF$_3$ | F |
| 1-CH$_3$—c-Pr | CF$_3$ | Br | 1-CH$_3$—c-Pr | OCH$_2$CF$_3$ | F |
| 2-CH$_3$—c-Pr | CF$_3$ | Br | 1,1'-bicyclopropyl-1-yl | OCH$_2$CF$_3$ | F |
| 1,1'-bicyclopropyl-1-yl | CF$_3$ | Br | H | OCH$_2$CF$_3$ | Cl |
| H | OCF$_2$H | F | Me | OCH$_2$CF$_3$ | Cl |
| Me | OCF$_2$H | F | t-Bu | OCH$_2$CF$_3$ | Cl |
| t-Bu | OCF$_2$H | F | 2-CH$_3$—c-Pr | OCH$_2$CF$_3$ | Cl |
| 1,1'-bicyclopropyl-1-yl | OCF$_2$H | F | 1,1'-bicyclopropyl-1-yl | OCH$_2$CF$_3$ | Cl |
| H | OCF$_2$H | Cl | H | OCH$_2$CF$_3$ | Br |
| Me | OCF$_2$H | Cl | Me | OCH$_2$CF$_3$ | Br |
| t-Bu | OCF$_2$H | Cl | t-Bu | OCH2CF$_3$ | Br |
| 1,1'-bicyclopropyl-2-yl | OCF$_2$H | Cl | 1-CH$_3$—c-Pr | OCH$_2$CF$_3$ | Br |
| H | OCF$_2$H | Br | 1,1'-bicyclopropyl-2-yl | OCH$_2$CF$_3$ | Br |
| Me | OCF$_2$H | Br | t-Bu | OCF$_2$H | Br |

| R$^2$ is Me, Y is Cl, R$^{16}$ is H and Z is CH. | | | R$^2$ is Me, Y is Cl, R$^{16}$ is H and Z is CH. | | |
|---|---|---|---|---|---|
| H | Br | F | H | Br | Cl |
| Me | Br | F | Me | Br | Cl |
| t-Bu | Br | F | t-Bu | Br | Cl |
| c-Pr | Br | F | c-Pr | Br | Cl |
| c-PrCH$_2$ | Br | F | c-PrCH$_2$ | Br | Cl |
| 1,1'-bicyclopropyl-2-yl | Br | F | 1,1'-bicyclopropyl-2-yl | Br | Cl |
| 1,1'-bicyclopropyl-1-yl | Br | F | 1,1'-bicyclopropyl-1-yl | Br | Cl |
| (1R,2S)-1,1'-bicyclopropyl-2-yl | Br | F | (1R,2S)-1,1'-bicyclopropyl-2-yl | Br | Cl |
| (1R,2R)-1,1'-bicyclopropyl-2-yl | Br | F | (1R,2R)-1,1'-bicyclopropyl-2-yl | Br | Cl |
| H | Br | Br | H | Cl | F |
| Me | Br | Br | Me | Cl | F |
| t-Bu | Br | Br | t-Bu | Cl | F |
| c-Pr | Br | Br | c-Pr | Cl | F |
| c-PrCH$_2$ | Br | Br | c-PrCH$_2$ | Cl | F |
| 1,1'-bicyclopropyl-2-yl | Br | Br | 1,1'-bicyclopropyl-2-yl | Cl | F |
| 1,1'-bicyclopropyl-1-yl | Br | Br | 1,1'-bicyclopropyl-1-yl | Cl | F |
| (1R,2R)-1,1'-bicyclopropyl-2-yl | Br | Br | (1R,2R)-1,1'-bicyclopropyl-2-yl | Cl | F |
| H | Cl | Cl | H | Cl | Br |
| Me | Cl | Cl | Me | Cl | Br |
| t-Bu | Cl | Cl | t-Bu | Cl | Br |
| c-Pr | Cl | Cl | c-Pr | Cl | Br |
| c-PrCH$_2$ | Cl | Cl | c-PrCH$_2$ | Cl | Br |
| 1,1'-bicyclopropyl-2-yl | Cl | Cl | 1,1'-bicyclopropyl-2-yl | Cl | Br |

TABLE 2-continued

| | | | | | |
|---|---|---|---|---|---|
| 1,1'-bicyclopropyl-1-yl | Cl | Cl | 1,1'-bicyclopropyl-1-yl | Cl | Br |
| (1S,2R)-1,1'-bicyclopropyl-2-yl | Cl | Cl | (1S,2R)-1,1'-bicyclopropyl-2-yl | Cl | Br |
| H | $CF_3$ | F | H | $CF_3$ | Cl |
| Me | $CF_3$ | F | Me | $CF_3$ | Cl |
| t-Bu | $CF_3$ | F | t-Bu | $CF_3$ | Cl |
| 2-$CH_3$—c-Pr | $CF_3$ | F | Me | $CF_3$ | Cl |
| 1,1'-bicyclopropyl-2-yl | $CF_3$ | F | Et | $CF_3$ | Br |
| Me | $OCH_2CF_3$ | F | c-Pr | $CF_3$ | Br |
| Et | $OCH_2CF_3$ | F | c-Pr$CH_2$ | $CF_3$ | Br |
| c-Pr | $OCH_2CF_3$ | F | 1,1'-bicyclopropyl-1-yl | $CF_3$ | Br |
| Me | $OCH_2CF_3$ | Cl | Me | $OCF_2H$ | F |
| c-Pr$CH_2$ | $OCH_2CF_3$ | Cl | Et | $OCF_2H$ | F |
| 1,1'-bicyclopropyl-1-yl | $OCH_2CF_3$ | Cl | c-Pr | $OCF_2H$ | Cl |
| Me | $OCH_2CF_3$ | Br | c-Pr$CH_2$ | $OCF_2H$ | Cl |
| Et | $OCH_2CF_3$ | Br | 1,1'-bicyclopropyl-1-yl | $OCF_2H$ | Cl |
| Et | $OCH_2CF_3$ | Br | Me | $OCF_2H$ | Br |
| c-Pr | $OCH_2CF_3$ | Br | Et | $OCF_2H$ | Br |

| $R^2$ is Me, Y is Cl, $R^{16}$ is F and Z is N. | | | $R^2$ is Me, Y is Cl, $R^{16}$ is F and Z is N. | | |
|---|---|---|---|---|---|
| H | Br | F | H | Br | Cl |
| Me | Br | F | Me | Br | Cl |
| t-Bu | Br | F | t-Bu | Br | Cl |
| c-Pr | Br | F | c-Pr | Br | Cl |
| c-Pr$CH_2$ | Br | F | c-Pr$CH_2$ | Br | Cl |
| 1,1'-bicyclopropyl-2-yl | Br | F | 1,1'-bicyclopropyl-2-yl | Br | Cl |
| 1,1'-bicyclopropyl-1-yl | Br | F | 1,1'-bicyclopropyl-1-yl | Br | Cl |
| H | Br | Br | H | Cl | F |
| Me | Br | Br | Me | Cl | F |
| t-Bu | Br | Br | t-Bu | Cl | F |
| c-Pr | Br | Br | c-Pr | Cl | F |
| c-Pr$CH_2$ | Br | Br | c-Pr$CH_2$ | Cl | F |
| 1,1'-bicyclopropyl-2-yl | Br | Br | 1,1'-bicyclopropyl-2-yl | Cl | F |
| (1R,2S)-1,1'-bicyclopropyl-2-yl | Br | Br | (1R,2S)-1,1'-bicyclopropyl-2-yl | Cl | F |
| H | Cl | Cl | H | Cl | Br |
| Me | Cl | Cl | Me | Cl | Br |
| t-Bu | Cl | Cl | t-Bu | Cl | Br |
| c-Pr | Cl | Cl | c-Pr | Cl | Br |
| c-Pr$CH_2$ | Cl | Cl | c-Pr$CH_2$ | Cl | Br |
| 1,1'-bicyclopropyl-2-yl | Cl | Cl | 1,1'-bicyclopropyl-2-yl | Cl | Br |
| 1,1'-bicyclopropyl-1-yl | Cl | Cl | 1,1'-bicyclopropyl-1-yl | Cl | Br |
| H | $CF_3$ | F | Me | $OCH_2CF_3$ | F |
| Me | $CF_3$ | F | Et | $OCH_2CF_3$ | F |
| t-Bu | $CF_3$ | F | c-Pr | $OCH_2CF_3$ | Cl |
| 2-$CH_3$—c-Pr | $CF_3$ | F | c-Pr$CH_2$ | $OCH_2CF_3$ | Cl |
| 1,1'-bicyclopropyl-2-yl | $CF_3$ | F | 1,1'-bicyclopropyl-1-yl | $OCH_2CF_3$ | Cl |
| H | $CF_3$ | Cl | Me | $OCH_2CF_3$ | Br |
| Me | $CF_3$ | Cl | Et | $OCH_2CF_3$ | Br |
| t-Bu | $CF_3$ | Cl | Me | $OCF_2H$ | F |
| c-Pr | $CF_3$ | Cl | Et | $OCF_2H$ | F |
| Me | $CF_3$ | Br | c-Pr | $OCF_2H$ | Cl |
| Et | $CF_3$ | Br | c-Pr$CH_2$ | $OCF_2H$ | Cl |
| c-Pr | $CF_3$ | Br | 1,1'-bicyclopropyl-2-yl | $OCF_2H$ | Cl |
| c-Pr$CH_2$ | $CF_3$ | Br | Me | $OCF_2H$ | Br |
| 1,1'-bicyclopropyl-1-yl | $CF_3$ | Br | Et | $OCF_2H$ | Br |

| $R^2$ is Me, Y is Cl, $R^{16}$ is Cl and Z is N. | | | $R^2$ is Me, Y is Cl, $R^{16}$ is Cl and Z is N. | | |
|---|---|---|---|---|---|
| H | Br | F | H | Br | Cl |
| Me | Br | F | Me | Br | Cl |
| t-Bu | Br | F | t-Bu | Br | Cl |
| c-Pr | Br | F | c-Pr | Br | Cl |
| c-Pr$CH_2$ | Br | F | c-Pr$CH_2$ | Br | Cl |
| 1,1'-bicyclopropyl-2-yl | Br | F | 1,1'-bicyclopropyl-2-yl | Br | Cl |
| 1,1'-bicyclopropyl-1-yl | Br | F | (1R,2S)-1,1'-bicyclopropyl-2-yl | Br | Cl |
| H | Br | Br | H | Cl | F |
| Me | Br | Br | Me | Cl | F |
| t-Bu | Br | Br | t-Bu | Cl | F |
| c-Pr | Br | Br | c-Pr | Cl | F |
| c-Pr$CH_2$ | Br | Br | c-Pr$CH_2$ | Cl | F |
| 1,1'-bicyclopropyl-1-yl | Br | Br | 1,1'-bicyclopropyl-2-yl | Cl | F |
| (1R,2R)-1,1'-bicyclopropyl-2-yl | Br | Br | (1R,2R)-1,1'-bicyclopropyl-2-yl | Cl | F |
| H | Cl | Br | H | Cl | Cl |
| Me | Cl | Br | Me | Cl | Cl |
| t-Bu | Cl | Br | t-Bu | Cl | Cl |
| c-Pr | Cl | Br | c-Pr | Cl | Cl |
| c-Pr$CH_2$ | Cl | Br | c-Pr$CH_2$ | Cl | Cl |
| 1,1'-bicyclopropyl-2-yl | Cl | Br | 1,1'-bicyclopropyl-2-yl | Cl | Cl |
| 1,1'-bicyclopropyl-1-yl | Cl | Br | 1,1'-bicyclopropyl-1-yl | Cl | Cl |
| H | $CF_3$ | F | Me | $OCH_2CF_3$ | F |

TABLE 2-continued

| | | | | | |
|---|---|---|---|---|---|
| Me | $CF_3$ | F | Et | $OCH_2CF_3$ | F |
| t-Bu | $CF_3$ | F | c-Pr | $OCH_2CF_3$ | Cl |
| 2-$CH_3$—c-Pr | $CF_3$ | F | c-$PrCH_2$ | $OCH_2CF_3$ | Cl |
| 1,1'-bicyclopropyl-2-yl | $CF_3$ | F | 1,1'-bicyclopropyl-1-yl | $OCH_2CF_3$ | Cl |
| 1,1'-bicyclopropyl-1-yl | $CF_3$ | F | Me | $OCH_2CF_3$ | Br |
| H | $CF_3$ | Cl | Et | $OCH_2CF_3$ | Br |
| Me | $CF_3$ | Cl | Me | $OCF_2H$ | F |
| t-Bu | $CF_3$ | Cl | Et | $OCF_2H$ | F |
| Me | $CF_3$ | Br | c-Pr | $OCF_2H$ | Cl |
| Et | $CF_3$ | Br | c-$PrCH_2$ | $OCF_2H$ | Cl |
| c-Pr | $CF_3$ | Br | 1,1'-bicyclopropyl-2-yl | $OCF_2H$ | F |
| c-$PrCH_2$ | $CF_3$ | Br | Me | $OCF_2H$ | Br |
| 1,1'-bicyclopropyl-1-yl | $CF_3$ | Br | Et | $OCF_2H$ | Br |

What is claimed is:

1. A method for preparing a compound of Formula 2

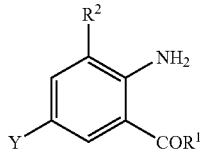

2 wherein

Y is Br;

$R^1$ is $NHR^3$;

$R^2$ is $CH_3$ or Cl; and $R^3$ is H, $C_1$-$C_4$ alkyl, cyclopropyl, cyclopropylcyclopropyl, cyclopropylmethyl or methylcyclopropyl;

comprising introducing (a) a gas containing bromine into (b) a liquid containing a compound of Formula 4

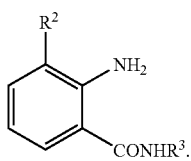

4

2. The method of claim 1 wherein $R^3$ is $CH_3$.

3. A method for preparing a compound of Formula 1

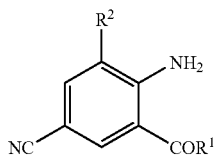

1 wherein $R^1$ is $NHR^3$;

$R^2$ is $CH_3$ or Cl; and $R^3$ is H, $C_1$-$C_4$ alkyl, cyclopropyl, cyclopropylcyclopropyl, cyclopropylmethyl or methylcyclopropyl;

comprising (A) preparing a compound of Formula 2

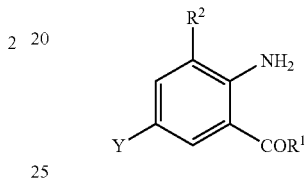

2 wherein Y is Br;

by introducing (a) a gas containing bromine into (b) a liquid containing a compound of Formula 4;

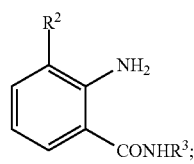

4 and (B) contacting (1) the compound of Formula 2 with (2) a metal cyanide reagent, (3) a copper(I) salt reagent, (4) an iodide salt reagent and (5) at least one compound of Formula 3

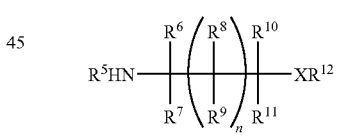

3 wherein

X is $NR^{13}$ or O;

$R^5$, $R^7$, $R^8$, $R^9$, $R^{11}$ and $R^{12}$ are independently H or $C_1$-$C_4$ alkyl;

$R^6$ and $R^{10}$ are independently H, $C_1$-$C_4$ alkyl or phenyl;

$R^{13}$ is H or methyl; and n is 0 or 1;

provided that:

(i) when n is 0, X is $NR^{13}$, and $R^5$, $R^{12}$ and $R^{13}$ are H, then at least two of $R^6$, $R^7$, $R^{10}$ and $R^{11}$ are other than H;

(ii) when n is 1, X is $NR^{13}$, and $R^5$, $R^{12}$, and $R^{13}$ are H, then at least two of $R^6$, $R^7$, $R^8$, $R^9$, $R^{10}$ and $R^{11}$ are other than H;

(iii) when n is 0, X is O, and $R^5$ and $R^{12}$ are H, then at least two of $R^6$, $R^7$, $R^{10}$ and $R^{11}$ are other than H;

(iv) when n is 1, X is O, and $R^5$ and $R^{12}$ are H, then at least two of $R^6$, $R^7$, $R^8$, $R^9$, $R^{10}$ and $R^{11}$ are other than H; and (v) when $R^2$ is Cl, then Y is Br.

* * * * *